(12) United States Patent
Baker et al.

(10) Patent No.: US 7,056,674 B2
(45) Date of Patent: Jun. 6, 2006

(54) PREDICTION OF LIKELIHOOD OF CANCER RECURRENCE

(75) Inventors: Joffre B. Baker, Montara, CA (US);
John L. Bryant, Pittsburgh, PA (US);
Soonmyung Paik, Pittsburgh, PA (US);
Steven Shak, Hillsborough, CA (US)

(73) Assignees: Genomic Health, Inc., Redwood City, CA (US); NSABP Foundation, Inc., Pittsburgh, PA (US)

( * ) Notice: Subject to any disclaimer, the term of this patent is extended or adjusted under 35 U.S.C. 154(b) by 48 days.

(21) Appl. No.: 10/872,063

(22) Filed: Jun. 17, 2004

(65) Prior Publication Data

US 2005/0079518 A1  Apr. 14, 2005

Related U.S. Application Data

(60) Provisional application No. 60/482,339, filed on Jun. 24, 2003.

(51) Int. Cl.
*C07H 21/04* (2006.01)
*C12Q 1/68* (2006.01)

(52) U.S. Cl. .................. 435/6; 435/91.1; 435/91.2; 536/23.1

(58) Field of Classification Search .................. 435/6, 435/91.1, 91.2, 287.2; 536/23.1, 24.3
See application file for complete search history.

(56) References Cited

U.S. PATENT DOCUMENTS

2003/0105000 A1 * 6/2003 Pero et al. ............... 514/12
2004/0209290 A1 * 10/2004 Cobleigh et al. ............ 435/6

FOREIGN PATENT DOCUMENTS

| WO | WO 99/02714 | 1/1999 |
|---|---|---|
| WO | WO 00/50595 | 8/2000 |
| WO | WO 00/55173 | 9/2000 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/083096 | 10/2003 |

OTHER PUBLICATIONS

Debouck et al. "DNA microarrays in drug discovery and development." Nature Genetics Supplement. vol. 21, pp. 48-50, Jan. 1999.*

Ahmad et al. "Stromelysin 3: An independent prognostic factor for relapse-free survival in node-positive breast cancer and demonstration of novel breast carcinoma cell expression." Am. J. of Path. vol. 152, No. 3, pp. 721-728, Mar. 1998.*

Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795, Nov. 20, 2001.

Golub et al., "Molecular Classification of Cancer: Class Discovery and Class Prediction by Gene Expression Monitoring", Science, vol. 286, pp. 531-537, Oct. 15, 1999.

Martin et al., "Linking Gene Expression Patterns to Therapeutic Groups in Breast Cancer", Cancer Research, vol. 60, pp. 2232-2238, Apr. 15, 2000.

Ramaswamy et al., "Multiclass cancer diagnosis using tumor gene expression signatures", Proceedings of the National Academy of Sciences of USA, vol. 98, No. 26, pp. 15149-15154, Dec. 18, 2001.

Sorlie et al., "Gene expression patterns of breast carcinomas distinguish tumor subclass with clinicl implications", Proceedings of the National Academy of Sciences of USA, vol. 98, No. 19, pp. 10869-10874, Sep. 11, 2001.

West et al., "Predicting the clinical status of human breast cancer by using gene expression profiles", Proceedings of the National Academy of Sciences of USA, vol. 98, No. 20, pp. 11462-11467, Sep. 25, 2001.

Yan et al., "Dissecting Complex Epigenetic Alterations in Breast Cancer Using CpG Island Microarrays", Cancer Research, vol. 61, pp. 8375-7380, Dec. 1, 2001.

Yeang et al., "Molecular classification of multiple tumor types", Bioinformatics, vol. 17, Suppl. 1, pp. S316-S322, 2001.

* cited by examiner

*Primary Examiner*—Jeanine A. Goldberg
(74) *Attorney, Agent, or Firm*—Ginger R. Dreger; Heller Ehrman LLP

(57) ABSTRACT

The present invention provides gene sets the expression of which is important in the diagnosis and/or prognosis of cancer, in particular of breast cancer.

10 Claims, No Drawings

```
                          SEQUENCE LISTING

<160> NUMBER OF SEQ ID NOS: 216

<210> SEQ ID NO 1
<211> LENGTH: 80
<212> TYPE: DNA
<213> ORGANISM: Artificial Sequence
<220> FEATURE:
<223> OTHER INFORMATION: PCR Amplicon

<400> SEQUENCE: 1
ggctcttgtg cgtactgtcc ttcgggctgg tgacagggaa gacatcactg agcctgccat      60
ctgtgctctt cgtcatctga                                                  80

<210> SEQ ID NO 2
<211> LENGTH: 81
<212> TYPE: DNA
<213> ORGANISM: Artificial Sequence
<220> FEATURE:
<223> OTHER INFORMATION: PCR Amplicon

<400> SEQUENCE: 2
cgttgtcagc acttggaata caagatggtt gccgggtcat gttaattggg aaaagaaca      60 gtccacagga agaggttgaa c                                                81

<210> SEQ ID NO 3
<211> LENGTH: 76
<212> TYPE: DNA
<213> ORGANISM: Artificial Sequence
<220> FEATURE:
<223> OTHER INFORMATION: PCR Amplicon

<400> SEQUENCE: 3
cctgcaaaag ggaacaagag cccttcgcct ccagatggct cccctgccgc caccccgag      60 atcagagtca accacg                                                      76
```

-continued

```
<210> SEQ ID NO 4
<211> LENGTH: 68
<212> TYPE: DNA
<213> ORGANISM: Artificial Sequence
<220> FEATURE:
<223> OTHER INFORMATION: PCR Amplicon

<400> SEQUENCE: 4
ccgaggttaa tccagcacgt atggggccaa gtgtaggctc ccagcaggaa ctgagagcgc      60
catgtctt                                                              68

<210> SEQ ID NO 5
<211> LENGTH: 65
<212> TYPE: DNA
<213> ORGANISM: Artificial Sequence
<220> FEATURE:
<223> OTHER INFORMATION: PCR Amplicon

<400> SEQUENCE: 5
tcagctgtga gctgcggata ccgcccggca atgggacctg ctcttaacct caaacctagg      60
accgt                                                                 65

<210> SEQ ID NO 6
<211> LENGTH: 84
<212> TYPE: DNA
<213> ORGANISM: Artificial Sequence
<220> FEATURE:
<223> OTHER INFORMATION: PCR Amplicon

<400> SEQUENCE: 6
ttcaggttgt tgcaggagac catgtacatg actgtctcca ttattgatcg gttcatgcag      60
aataattgtg tgcccaagaa gatg                                            84

<210> SEQ ID NO 7
<211> LENGTH: 82
<212> TYPE: DNA
<213> ORGANISM: Artificial Sequence
<220> FEATURE:
<223> OTHER INFORMATION: PCR Amplicon

<400> SEQUENCE: 7
atgctgtggc tccttcctaa ctggggcttt cttgacatgt aggttgcttg gtaataacct      60
ttttgtatat cacaatttgg gt                                              82

<210> SEQ ID NO 8
<211> LENGTH: 68
<212> TYPE: DNA
<213> ORGANISM: Artificial Sequence
<220> FEATURE:
<223> OTHER INFORMATION: PCR Amplicon

<400> SEQUENCE: 8
tggattggag ttctgggaat gtactggccg tggcactgga caacagtgtg tacctgtgga      60
gtgcaagc                                                              68

<210> SEQ ID NO 9
<211> LENGTH: 81
<212> TYPE: DNA
<213> ORGANISM: Artificial Sequence
<220> FEATURE:
<223> OTHER INFORMATION: PCR Amplicon
```

```
<400> SEQUENCE: 9
tgagtgtccc ccggtatctt ccccgccctg ccaatcccga tgaaattgga aattttattg      60
atgaaaatct gaaagcggct g                                                81

<210> SEQ ID NO 10
<211> LENGTH: 77
<212> TYPE: DNA
<213> ORGANISM: Artificial Sequence
<220> FEATURE:
<223> OTHER INFORMATION: PCR Amplicon

<400> SEQUENCE: 10
tgacaatcag cacacctgca ttcaccgctc ggaagagggc ctgagctgca tgaataagga      60
tcacggctgt agtcaca                                                     77

<210> SEQ ID NO 11
<211> LENGTH: 72
<212> TYPE: DNA
<213> ORGANISM: Artificial Sequence
<220> FEATURE:
<223> OTHER INFORMATION: PCR Amplicon

<400> SEQUENCE: 11
tgcctgtggt gggaagctca gtaactggga accaaaggat gatgctatgt cagaacaccg      60
gaggcatttt cc                                                          72

<210> SEQ ID NO 12
<211> LENGTH: 84
<212> TYPE: DNA
<213> ORGANISM: Artificial Sequence
<220> FEATURE:
<223> OTHER INFORMATION: PCR Amplicon

<400> SEQUENCE: 12
tccctccact cggaaggact atcctgctgc caagagggtc aagttggaca gtgtcagagt      60
cctgagacag atcagcaaca accg                                             84

<210> SEQ ID NO 13
<211> LENGTH: 67
<212> TYPE: DNA
<213> ORGANISM: Artificial Sequence
<220> FEATURE:
<223> OTHER INFORMATION: PCR Amplicon

<400> SEQUENCE: 13
tgtctcactg agcgagcaga atctggtgga ctgttcgcgt cctcaaggca atcagggctg      60
caatggt                                                                67

<210> SEQ ID NO 14
<211> LENGTH: 74
<212> TYPE: DNA
<213> ORGANISM: Artificial Sequence
<220> FEATURE:
<223> OTHER INFORMATION: PCR Amplicon

<400> SEQUENCE: 14 tccatttttct acctgttaac cttcatcatt ttgtgcaggc cctggaagca aagagaggaa     60
gggaccgact gcat                                                        74
```

<210> SEQ ID NO 15
<211> LENGTH: 84
<212> TYPE: DNA
<213> ORGANISM: Artificial Sequence
<220> FEATURE:
<223> OTHER INFORMATION: PCR Amplicon

<400> SEQUENCE: 15
ctctgagaca gtgcttcgat gactttgcag acttggtgcc ctttgactcc tgggagccgc    60
tcatgaggaa gttgggcctc atgg                                          84

<210> SEQ ID NO 16
<211> LENGTH: 75
<212> TYPE: DNA
<213> ORGANISM: Artificial Sequence
<220> FEATURE:
<223> OTHER INFORMATION: PCR Amplicon

<400> SEQUENCE: 16
gggccctcca gaacaatgat gggctttatg atcctgactg cgatgagagc gggctcttta    60
aggccaagca gtgca                                                    75

<210> SEQ ID NO 17
<211> LENGTH: 68
<212> TYPE: DNA
<213> ORGANISM: Artificial Sequence
<220> FEATURE:
<223> OTHER INFORMATION: PCR Amplicon

<400> SEQUENCE: 17
cgtggtgccc ctctatgacc tgctgctgga gatgctggac gcccaccgcc tacatgcgcc    60
cactagcc                                                            68

<210> SEQ ID NO 18
<211> LENGTH: 74
<212> TYPE: DNA
<213> ORGANISM: Artificial Sequence
<220> FEATURE:
<223> OTHER INFORMATION: PCR Amplicon

<400> SEQUENCE: 18
cacgggacat tcaccacatc gactactata aaaagacaac caacggccga ctgcctgtga    60
agtggatggc accc                                                     74

<210> SEQ ID NO 19
<211> LENGTH: 82
<212> TYPE: DNA
<213> ORGANISM: Artificial Sequence
<220> FEATURE:
<223> OTHER INFORMATION: PCR Amplicon

<400> SEQUENCE: 19
ccaccccgag caaatctgtc ctccccagaa ccctgaatc ctggaggctc acgccccag      60 ccaaagtagg gggactggat tt                                            82

<210> SEQ ID NO 20
<211> LENGTH: 67
<212> TYPE: DNA
<213> ORGANISM: Artificial Sequence
<220> FEATURE:
<223> OTHER INFORMATION: PCR Amplicon

```
-continued

<400> SEQUENCE: 20
ccatctgcat ccatcttgtt tgggctcccc acccttgaga agtgcctcag ataatacctt      60
ggtggcc                                                                67

<210> SEQ ID NO 21
<211> LENGTH: 86
<212> TYPE: DNA
<213> ORGANISM: Artificial Sequence
<220> FEATURE:
<223> OTHER INFORMATION: PCR Amplicon

<400> SEQUENCE: 21
aagctatgag gaaaagaagt acacgatggg ggacgctcct gattatgaca gaagccagtg      60
gctgaatgaa aaattcaagc tgggcc                                           86

<210> SEQ ID NO 22
<211> LENGTH: 76
<212> TYPE: DNA
<213> ORGANISM: Artificial Sequence
<220> FEATURE:
<223> OTHER INFORMATION: PCR Amplicon

<400> SEQUENCE: 22
caatgccatc ttgcgctaca tcgctcgcaa gcacaacatg tgtggtgaga ctgaagaaga      60
aaagattcga gtggac                                                      76

<210> SEQ ID NO 23
<211> LENGTH: 70
<212> TYPE: DNA
<213> ORGANISM: Artificial Sequence
<220> FEATURE:
<223> OTHER INFORMATION: PCR Amplicon

<400> SEQUENCE: 23
cggtgtgaga agtgcagcaa gccctgtgcc cgagtgtgct atggtctggg catggagcac      60
ttgcgagagg                                                             70

<210> SEQ ID NO 24
<211> LENGTH: 84
<212> TYPE: DNA
<213> ORGANISM: Artificial Sequence
<220> FEATURE:
<223> OTHER INFORMATION: PCR Amplicon

<400> SEQUENCE: 24
caagggagcg accaactgat cgcacacatg ctttgtttgg atatggagtg aacacaatta      60
tgtaccaaat ttaacttggc aaac                                             84

<210> SEQ ID NO 25
<211> LENGTH: 70
<212> TYPE: DNA
<213> ORGANISM: Artificial Sequence
<220> FEATURE:
<223> OTHER INFORMATION: PCR Amplicon

<400> SEQUENCE: 25
agaaccgcaa ggtgagcaag gtggagattc tccagcacgt catcgactac atcagggacc      60
ttcagttgga                                                             70
```

<210> SEQ ID NO 26
<211> LENGTH: 83
<212> TYPE: DNA
<213> ORGANISM: Artificial Sequence
<220> FEATURE:
<223> OTHER INFORMATION: PCR Amplicon

<400> SEQUENCE: 26
gcatggtagc cgaagatttc acagtcaaaa tcggagattt tggtatgacg cgagatatct    60
atgagacaga ctattaccgg aaa                                            83

<210> SEQ ID NO 27
<211> LENGTH: 79
<212> TYPE: DNA
<213> ORGANISM: Artificial Sequence
<220> FEATURE:
<223> OTHER INFORMATION: PCR Amplicon

<400> SEQUENCE: 27
gatatgattg gtcgctgctt tgtgctcagc caggacctgg ccatccggga tgagttggat    60
ggtggggaat ggaagttct                                                 79

<210> SEQ ID NO 28
<211> LENGTH: 80
<212> TYPE: DNA
<213> ORGANISM: Artificial Sequence
<220> FEATURE:
<223> OTHER INFORMATION: PCR Amplicon

<400> SEQUENCE: 28
cggactttgg gtgcgacttg acgagcggtg gttcgacaag tggccttgcg ggccggatcg    60
tcccagtgga agagttgtaa                                                80

<210> SEQ ID NO 29
<211> LENGTH: 78
<212> TYPE: DNA
<213> ORGANISM: Artificial Sequence
<220> FEATURE:
<223> OTHER INFORMATION: PCR Amplicon

<400> SEQUENCE: 29
gcccagaggc tccatcgtcc atcctcttcc tccccagtcg gctgaactct cccctttgtct   60 gcactgttca aacctctg                                                  78

<210> SEQ ID NO 30
<211> LENGTH: 77
<212> TYPE: DNA
<213> ORGANISM: Artificial Sequence
<220> FEATURE:
<223> OTHER INFORMATION: PCR Amplicon

<400> SEQUENCE: 30
ccacctcgcc atgatttttc ctttgaccgg gtattcccac caggaagtgg acaggatgaa    60
gtgtttgaag agattgc                                                   77

<210> SEQ ID NO 31
<211> LENGTH: 69
<212> TYPE: DNA
<213> ORGANISM: Artificial Sequence
<220> FEATURE:
<223> OTHER INFORMATION: PCR Amplicon

```
<400> SEQUENCE: 31
tcagtggaga aggagttgga ccagtcaaca tctctgttgt cacaagcagt gtttcctctg    60
gatatggca                                                           69

<210> SEQ ID NO 32
<211> LENGTH: 66
<212> TYPE: DNA
<213> ORGANISM: Artificial Sequence
<220> FEATURE:
<223> OTHER INFORMATION: PCR Amplicon

<400> SEQUENCE: 32
tgcaaacgct ggtgtcacag ccagcccccc aactgacctc atctggaaga accagaactc    60
gtgggg                                                              66

<210> SEQ ID NO 33
<211> LENGTH: 75
<212> TYPE: DNA
<213> ORGANISM: Artificial Sequence
<220> FEATURE:
<223> OTHER INFORMATION: PCR Amplicon

<400> SEQUENCE: 33
gacttttgcc cgctaccttt cattccggcg tgacaacaat gagctgttgc tcttcatact    60
gaagcagtta gtggc                                                    75

<210> SEQ ID NO 34
<211> LENGTH: 82
<212> TYPE: DNA
<213> ORGANISM: Artificial Sequence
<220> FEATURE:
<223> OTHER INFORMATION: PCR Amplicon

<400> SEQUENCE: 34
tgatggtcct atgtgtcaca ttcatcacag gtttcatacc aacacaggct tcagcacttc    60
ctttggtgtg tttcctgtcc ca                                            82

<210> SEQ ID NO 35
<211> LENGTH: 65
<212> TYPE: DNA
<213> ORGANISM: Artificial Sequence
<220> FEATURE:
<223> OTHER INFORMATION: PCR Amplicon

<400> SEQUENCE: 35
aacccggcga tcgaaaagat tcttaggaac gccgtaccag ccgcgtctct caggacagca    60
ggccc                                                               65

<210> SEQ ID NO 36
<211> LENGTH: 78
<212> TYPE: DNA
<213> ORGANISM: Artificial Sequence
<220> FEATURE:
<223> OTHER INFORMATION: PCR Amplicon

<400> SEQUENCE: 36
ccaacgcttg ccaaatcctg acaattcaga accagctctc tgtgacccca atttgagttt    60
tgatgctgtc actaccgt                                                 78
```

```
<210> SEQ ID NO 37
<211> LENGTH: 67
<212> TYPE: DNA
<213> ORGANISM: Artificial Sequence
<220> FEATURE:
<223> OTHER INFORMATION: PCR Amplicon

<400> SEQUENCE: 37
gagaaccaat ctcaccgaca ggcagctggc agaggaatac ctgtaccgct atggttacac      60
tcgggtg                                                               67

<210> SEQ ID NO 38
<211> LENGTH: 74
<212> TYPE: DNA
<213> ORGANISM: Artificial Sequence
<220> FEATURE:
<223> OTHER INFORMATION: PCR Amplicon

<400> SEQUENCE: 38
gccgagatcg ccaagatgtt gccagggagg acagacaatg ctgtgaagaa tcactggaac      60
tctaccatca aaag                                                       74

<210> SEQ ID NO 39
<211> LENGTH: 79
<212> TYPE: DNA
<213> ORGANISM: Artificial Sequence
<220> FEATURE:
<223> OTHER INFORMATION: PCR Amplicon

<400> SEQUENCE: 39
gtgaggcagc gcgactctgg cgactggccg gccatgcctt cccgggctga ggactatgaa      60
gtgttgtaca ccattggca                                                  79

<210> SEQ ID NO 40
<211> LENGTH: 74
<212> TYPE: DNA
<213> ORGANISM: Artificial Sequence
<220> FEATURE:
<223> OTHER INFORMATION: PCR Amplicon

<400> SEQUENCE: 40
ccaaccctgc agactccaag cctgggacca tccgtggaga cttctgcata caagttggca      60
ggaacattat acat                                                       74

<210> SEQ ID NO 41
<211> LENGTH: 73
<212> TYPE: DNA
<213> ORGANISM: Artificial Sequence
<220> FEATURE:
<223> OTHER INFORMATION: PCR Amplicon

<400> SEQUENCE: 41
ggctgtggct gaggctgtag catctctgct ggaggtgaga cactctggga actgatttga      60
cctcgaatgc tcc                                                        73

<210> SEQ ID NO 42
<211> LENGTH: 71
<212> TYPE: DNA
<213> ORGANISM: Artificial Sequence
<220> FEATURE:
<223> OTHER INFORMATION: PCR Amplicon
```

```
<400> SEQUENCE: 42
gaaggtgttg gaggcactca aggacctcat caacgaggcc tgctgggata ttagctccag    60
cggtgtaaac c                                                        71

<210> SEQ ID NO 43
<211> LENGTH: 85
<212> TYPE: DNA
<213> ORGANISM: Artificial Sequence
<220> FEATURE:
<223> OTHER INFORMATION: PCR Amplicon

<400> SEQUENCE: 43
gcatcaggct gtcattatgg tgtccttacc tgtgggagct gtaaggtctt ctttaagagg    60
gcaatggaag ggcagcacaa ctact                                         85

<210> SEQ ID NO 44
<211> LENGTH: 76
<212> TYPE: DNA
<213> ORGANISM: Artificial Sequence
<220> FEATURE:
<223> OTHER INFORMATION: PCR Amplicon

<400> SEQUENCE: 44
gggacggtgt tcacattcaa gacgaatcgc cagtctccca actatcgcgt gatcaacatt    60
gacttctggg atcctg                                                   76

<210> SEQ ID NO 45
<211> LENGTH: 74
<212> TYPE: DNA
<213> ORGANISM: Artificial Sequence
<220> FEATURE:
<223> OTHER INFORMATION: PCR Amplicon

<400> SEQUENCE: 45
ggctactctg atctatgttg ataaggaaaa tggagaacca ggcacccgtg tggttgctaa    60
ggatgggctg aagc                                                     74

<210> SEQ ID NO 46
<211> LENGTH: 75
<212> TYPE: DNA
<213> ORGANISM: Artificial Sequence
<220> FEATURE:
<223> OTHER INFORMATION: PCR Amplicon

<400> SEQUENCE: 46
ccattctatc atcaacgggt acaaacgagt cctggccttg tctgtggaga cggattacac    60
cttcccactt gctga                                                    75

<210> SEQ ID NO 47
<211> LENGTH: 79
<212> TYPE: DNA
<213> ORGANISM: Artificial Sequence
<220> FEATURE:
<223> OTHER INFORMATION: PCR Amplicon

<400> SEQUENCE: 47
ggctggtcgg cagagagtag cctgcaacat tcggccgtgg tttacatgag tttaccctc    60 aatcccaaac ctttcctca                                                79
```

```
<210> SEQ ID NO 48
<211> LENGTH: 64
<212> TYPE: DNA
<213> ORGANISM: Artificial Sequence
<220> FEATURE:
<223> OTHER INFORMATION: PCR Amplicon

<400> SEQUENCE: 48
cctgaacatg aaggagctga agctgctgca gaccatcggg aaggggagt tcggagacgt    60 gatg                                                                64

<210> SEQ ID NO 49
<211> LENGTH: 69
<212> TYPE: DNA
<213> ORGANISM: Artificial Sequence
<220> FEATURE:
<223> OTHER INFORMATION: PCR Amplicon

<400> SEQUENCE: 49
catcttccag gaggaccact ctctgtggca ccctggacta cctgcccct gaaatgattg    60 aaggtcgga                                                           69

<210> SEQ ID NO 50
<211> LENGTH: 90
<212> TYPE: DNA
<213> ORGANISM: Artificial Sequence
<220> FEATURE:
<223> OTHER INFORMATION: PCR Amplicon

<400> SEQUENCE: 50
cctggaggct gcaacatacc tcaatcctgt cccaggccgg atcctcctga agcccttttc    60
gcagcactgc tatcctccaa agccattgta                                    90

<210> SEQ ID NO 51
<211> LENGTH: 79
<212> TYPE: DNA
<213> ORGANISM: Artificial Sequence
<220> FEATURE:
<223> OTHER INFORMATION: PCR Amplicon

<400> SEQUENCE: 51
tgttttgatt cccgggctta ccaggtgaga agtgagggag gaagaaggca gtgtcccttt    60
tgctagagct gacagcttg                                                79

<210> SEQ ID NO 52
<211> LENGTH: 68
<212> TYPE: DNA
<213> ORGANISM: Artificial Sequence
<220> FEATURE:
<223> OTHER INFORMATION: PCR Amplicon

<400> SEQUENCE: 52
gccaactgct ttcatttgtg agggatctga accaatacag agcagacata aaggaaatgg    60
gcctgagt                                                            68

<210> SEQ ID NO 53
<211> LENGTH: 72
<212> TYPE: DNA
<213> ORGANISM: Artificial Sequence
<220> FEATURE:
<223> OTHER INFORMATION: PCR Amplicon
```

```
<400> SEQUENCE: 53
aatccaaggg ggagagtgat gacttccata tggactttga ctcagctgtg gctcctcggg      60
caaaatctgt ac                                                          72

<210> SEQ ID NO 54
<211> LENGTH: 65
<212> TYPE: DNA
<213> ORGANISM: Artificial Sequence
<220> FEATURE:
<223> OTHER INFORMATION: PCR Amplicon

<400> SEQUENCE: 54
gcctcggtgt gcctttcaac atcgccagct acgccctgct cacgtacatg attgcgcaca      60
tcacg                                                                  65

<210> SEQ ID NO 55
<211> LENGTH: 22
<212> TYPE: DNA
<213> ORGANISM: Artificial Sequence
<220> FEATURE:
<223> OTHER INFORMATION: PCR primer-probe

<400> SEQUENCE: 55
ggctcttgtg cgtactgtcc tt                                               22

<210> SEQ ID NO 56
<211> LENGTH: 23
<212> TYPE: DNA
<213> ORGANISM: Artificial Sequence
<220> FEATURE:
<223> OTHER INFORMATION: PCR primer-probe

<400> SEQUENCE: 56
tcagatgacg aagagcacag atg                                              23

<210> SEQ ID NO 57
<211> LENGTH: 29
<212> TYPE: DNA
<213> ORGANISM: Artificial Sequence
<220> FEATURE:
<223> OTHER INFORMATION: PCR primer-probe

<400> SEQUENCE: 57
aggctcagtg atgtcttccc tgtcaccag                                        29

<210> SEQ ID NO 58
<211> LENGTH: 23
<212> TYPE: DNA
<213> ORGANISM: Artificial Sequence
<220> FEATURE:
<223> OTHER INFORMATION: PCR primer-probe

<400> SEQUENCE: 58
cgttgtcagc acttggaata caa                                              23

<210> SEQ ID NO 59
<211> LENGTH: 24
<212> TYPE: DNA
<213> ORGANISM: Artificial Sequence
<220> FEATURE:
<223> OTHER INFORMATION: PCR primer-probe

<400> SEQUENCE: 59
gttcaacctc ttcctgtgga ctgt                                             24
```

```
<210> SEQ ID NO 60
<211> LENGTH: 26
<212> TYPE: DNA
<213> ORGANISM: Artificial Sequence
<220> FEATURE:
<223> OTHER INFORMATION: PCR primer-probe

<400> SEQUENCE: 60
cccaattaac atgacccggc aaccat                                26

<210> SEQ ID NO 61
<211> LENGTH: 20
<212> TYPE: DNA
<213> ORGANISM: Artificial Sequence
<220> FEATURE:
<223> OTHER INFORMATION: PCR primer-probe

<400> SEQUENCE: 61
cctgcaaaag ggaacaagag                                       20

<210> SEQ ID NO 62
<211> LENGTH: 20
<212> TYPE: DNA
<213> ORGANISM: Artificial Sequence
<220> FEATURE:
<223> OTHER INFORMATION: PCR primer-probe

<400> SEQUENCE: 62
cgtggttgac tctgatctcg                                       20

<210> SEQ ID NO 63
<211> LENGTH: 21
<212> TYPE: DNA
<213> ORGANISM: Artificial Sequence
<220> FEATURE:
<223> OTHER INFORMATION: PCR primer-probe

<400> SEQUENCE: 63
cttcgcctcc agatggctcc c                                     21

<210> SEQ ID NO 64
<211> LENGTH: 21
<212> TYPE: DNA
<213> ORGANISM: Artificial Sequence
<220> FEATURE:
<223> OTHER INFORMATION: PCR primer-probe

<400> SEQUENCE: 64
ccgaggttaa tccagcacgt a                                     21

<210> SEQ ID NO 65
<211> LENGTH: 21
<212> TYPE: DNA
<213> ORGANISM: Artificial Sequence
<220> FEATURE:
<223> OTHER INFORMATION: PCR primer-probe

<400> SEQUENCE: 65
aagacatggc gctctcagtt c                                     21

<210> SEQ ID NO 66
<211> LENGTH: 23
<212> TYPE: DNA
<213> ORGANISM: Artificial Sequence
<220> FEATURE:
<223> OTHER INFORMATION: PCR primer-probe
```

```
<400> SEQUENCE: 66
tgctgggagc ctacacttgg ccc                                            23

<210> SEQ ID NO 67
<211> LENGTH: 20
<212> TYPE: DNA
<213> ORGANISM: Artificial Sequence
<220> FEATURE:
<223> OTHER INFORMATION: PCR primer-probe

<400> SEQUENCE: 67
tcagctgtga gctgcggata                                                20

<210> SEQ ID NO 68
<211> LENGTH: 24
<212> TYPE: DNA
<213> ORGANISM: Artificial Sequence
<220> FEATURE:
<223> OTHER INFORMATION: PCR primer-probe

<400> SEQUENCE: 68
acggtcctag gtttgaggtt aaga                                           24

<210> SEQ ID NO 69
<211> LENGTH: 19
<212> TYPE: DNA
<213> ORGANISM: Artificial Sequence
<220> FEATURE:
<223> OTHER INFORMATION: PCR primer-probe

<400> SEQUENCE: 69
caggtcccat tgccgggcg                                                 19

<210> SEQ ID NO 70
<211> LENGTH: 20
<212> TYPE: DNA
<213> ORGANISM: Artificial Sequence
<220> FEATURE:
<223> OTHER INFORMATION: PCR primer-probe

<400> SEQUENCE: 70
ttcaggttgt tgcaggagac                                                20

<210> SEQ ID NO 71
<211> LENGTH: 20
<212> TYPE: DNA
<213> ORGANISM: Artificial Sequence
<220> FEATURE:
<223> OTHER INFORMATION: PCR primer-probe

<400> SEQUENCE: 71
catcttcttg ggcacacaat                                                20

<210> SEQ ID NO 72
<211> LENGTH: 27
<212> TYPE: DNA
<213> ORGANISM: Artificial Sequence
<220> FEATURE:
<223> OTHER INFORMATION: PCR primer-probe

<400> SEQUENCE: 72
tgtctccatt attgatcggt tcatgca                                        27
```

```
<210> SEQ ID NO 73
<211> LENGTH: 22
<212> TYPE: DNA
<213> ORGANISM: Artificial Sequence
<220> FEATURE:
<223> OTHER INFORMATION: PCR primer-probe

<400> SEQUENCE: 73
atgctgtggc tccttcctaa ct                                    22

<210> SEQ ID NO 74
<211> LENGTH: 27
<212> TYPE: DNA
<213> ORGANISM: Artificial Sequence
<220> FEATURE:
<223> OTHER INFORMATION: PCR primer-probe

<400> SEQUENCE: 74
acccaaattg tgatatacaa aaaggtt                               27

<210> SEQ ID NO 75
<211> LENGTH: 30
<212> TYPE: DNA
<213> ORGANISM: Artificial Sequence
<220> FEATURE:
<223> OTHER INFORMATION: PCR primer-probe

<400> SEQUENCE: 75
taccaagcaa cctacatgtc aagaaagccc                            30

<210> SEQ ID NO 76
<211> LENGTH: 21
<212> TYPE: DNA
<213> ORGANISM: Artificial Sequence
<220> FEATURE:
<223> OTHER INFORMATION: PCR primer-probe

<400> SEQUENCE: 76
tggattggag ttctgggaat g                                     21

<210> SEQ ID NO 77
<211> LENGTH: 22
<212> TYPE: DNA
<213> ORGANISM: Artificial Sequence
<220> FEATURE:
<223> OTHER INFORMATION: PCR primer-probe

<400> SEQUENCE: 77
gcttgcactc cacaggtaca ca                                    22

<210> SEQ ID NO 78
<211> LENGTH: 23
<212> TYPE: DNA
<213> ORGANISM: Artificial Sequence
<220> FEATURE:
<223> OTHER INFORMATION: PCR primer-probe

<400> SEQUENCE: 78
actggccgtg gcactggaca aca                                   23

<210> SEQ ID NO 79
<211> LENGTH: 21
<212> TYPE: DNA
<213> ORGANISM: Artificial Sequence
<220> FEATURE:
<223> OTHER INFORMATION: PCR primer-probe
```

-continued

<400> SEQUENCE: 79
tgagtgtccc ccggtatctt c                                    21

<210> SEQ ID NO 80
<211> LENGTH: 21
<212> TYPE: DNA
<213> ORGANISM: Artificial Sequence
<220> FEATURE:
<223> OTHER INFORMATION: PCR primer-probe

<400> SEQUENCE: 80
cagccgcttt cagattttca t                                    21

<210> SEQ ID NO 81
<211> LENGTH: 27
<212> TYPE: DNA
<213> ORGANISM: Artificial Sequence
<220> FEATURE:
<223> OTHER INFORMATION: PCR primer-probe

<400> SEQUENCE: 81
tgccaatccc gatgaaattg gaaattt                              27

<210> SEQ ID NO 82
<211> LENGTH: 21
<212> TYPE: DNA
<213> ORGANISM: Artificial Sequence
<220> FEATURE:
<223> OTHER INFORMATION: PCR primer-probe

<400> SEQUENCE: 82
tgacaatcag cacacctgca t                                    21

<210> SEQ ID NO 83
<211> LENGTH: 23
<212> TYPE: DNA
<213> ORGANISM: Artificial Sequence
<220> FEATURE:
<223> OTHER INFORMATION: PCR primer-probe

<400> SEQUENCE: 83
tgtgactaca gccgtgatcc tta                                  23

<210> SEQ ID NO 84
<211> LENGTH: 20
<212> TYPE: DNA
<213> ORGANISM: Artificial Sequence
<220> FEATURE:
<223> OTHER INFORMATION: PCR primer-probe

<400> SEQUENCE: 84
caggccctct tccgagcggt                                      20

<210> SEQ ID NO 85
<211> LENGTH: 18
<212> TYPE: DNA
<213> ORGANISM: Artificial Sequence
<220> FEATURE:
<223> OTHER INFORMATION: PCR primer-probe

<400> SEQUENCE: 85
tgcctgtggt gggaagct                                        18

<210> SEQ ID NO 86
<211> LENGTH: 19
<212> TYPE: DNA
<213> ORGANISM: Artificial Sequence
<220> FEATURE:
<223> OTHER INFORMATION: PCR primer-probe

<400> SEQUENCE: 86
ggaaaatgcc tccggtgtt                                               19

<210> SEQ ID NO 87
<211> LENGTH: 30
<212> TYPE: DNA
<213> ORGANISM: Artificial Sequence
<220> FEATURE:
<223> OTHER INFORMATION: PCR primer-probe

<400> SEQUENCE: 87
tgacatagca tcatcctttg gttcccagtt                                   30

<210> SEQ ID NO 88
<211> LENGTH: 21
<212> TYPE: DNA
<213> ORGANISM: Artificial Sequence
<220> FEATURE:
<223> OTHER INFORMATION: PCR primer-probe

<400> SEQUENCE: 88
tccctccact cggaaggact a                                            21

<210> SEQ ID NO 89
<211> LENGTH: 22
<212> TYPE: DNA
<213> ORGANISM: Artificial Sequence
<220> FEATURE:
<223> OTHER INFORMATION: PCR primer-probe

<400> SEQUENCE: 89
cggttgttgc tgatctgtct ca                                           22

<210> SEQ ID NO 90
<211> LENGTH: 27
<212> TYPE: DNA
<213> ORGANISM: Artificial Sequence
<220> FEATURE:
<223> OTHER INFORMATION: PCR primer-probe

<400> SEQUENCE: 90
tctgacactg tccaacttga ccctctt                                      27

<210> SEQ ID NO 91
<211> LENGTH: 21
<212> TYPE: DNA
<213> ORGANISM: Artificial Sequence
<220> FEATURE:
<223> OTHER INFORMATION: PCR primer-probe

<400> SEQUENCE: 91
tgtctcactg agcgagcaga a                                            21

<210> SEQ ID NO 92
<211> LENGTH: 19
<212> TYPE: DNA
<213> ORGANISM: Artificial Sequence
<220> FEATURE:
<223> OTHER INFORMATION: PCR primer-probe

```
<400> SEQUENCE: 92
accattgcag ccctgattg                                                19

<210> SEQ ID NO 93
<211> LENGTH: 24
<212> TYPE: DNA
<213> ORGANISM: Artificial Sequence
<220> FEATURE:
<223> OTHER INFORMATION: PCR primer-probe

<400> SEQUENCE: 93
cttgaggacg cgaacagtcc acca                                          24

<210> SEQ ID NO 94
<211> LENGTH: 27
<212> TYPE: DNA
<213> ORGANISM: Artificial Sequence
<220> FEATURE:
<223> OTHER INFORMATION: PCR primer-probe

<400> SEQUENCE: 94
tccattttct acctgttaac cttcatc                                       27

<210> SEQ ID NO 95
<211> LENGTH: 19
<212> TYPE: DNA
<213> ORGANISM: Artificial Sequence
<220> FEATURE:
<223> OTHER INFORMATION: PCR primer-probe

<400> SEQUENCE: 95
atgcagtcgg tcccttcct                                                19

<210> SEQ ID NO 96
<211> LENGTH: 23
<212> TYPE: DNA
<213> ORGANISM: Artificial Sequence
<220> FEATURE:
<223> OTHER INFORMATION: PCR primer-probe

<400> SEQUENCE: 96
ttgcttccag ggcctgcaca aaa                                           23

<210> SEQ ID NO 97
<211> LENGTH: 24
<212> TYPE: DNA
<213> ORGANISM: Artificial Sequence
<220> FEATURE:
<223> OTHER INFORMATION: PCR primer-probe

<400> SEQUENCE: 97
ctctgagaca gtgcttcgat gact                                          24

<210> SEQ ID NO 98
<211> LENGTH: 19
<212> TYPE: DNA
<213> ORGANISM: Artificial Sequence
<220> FEATURE:
<223> OTHER INFORMATION: PCR primer-probe

<400> SEQUENCE: 98
ccatgaggcc caacttcct                                                19
```

```
<210> SEQ ID NO 99
<211> LENGTH: 23
<212> TYPE: DNA
<213> ORGANISM: Artificial Sequence
<220> FEATURE:
<223> OTHER INFORMATION: PCR primer-probe

<400> SEQUENCE: 99
cagacttggt gcccttTgac tcc                                              23

<210> SEQ ID NO 100
<211> LENGTH: 20
<212> TYPE: DNA
<213> ORGANISM: Artificial Sequence
<220> FEATURE:
<223> OTHER INFORMATION: PCR primer-probe

<400> SEQUENCE: 100
gggccctcca gaacaatgat                                                  20

<210> SEQ ID NO 101
<211> LENGTH: 21
<212> TYPE: DNA
<213> ORGANISM: Artificial Sequence
<220> FEATURE:
<223> OTHER INFORMATION: PCR primer-probe

<400> SEQUENCE: 101
tgcactgctt ggccttaaag a                                                21

<210> SEQ ID NO 102
<211> LENGTH: 25
<212> TYPE: DNA
<213> ORGANISM: Artificial Sequence
<220> FEATURE:
<223> OTHER INFORMATION: PCR primer-probe

<400> SEQUENCE: 102
ccgctctcat cgcagtcagg atcat                                            25

<210> SEQ ID NO 103
<211> LENGTH: 19
<212> TYPE: DNA
<213> ORGANISM: Artificial Sequence
<220> FEATURE:
<223> OTHER INFORMATION: PCR primer-probe

<400> SEQUENCE: 103
cgtggtgccc ctctatgac                                                   19

<210> SEQ ID NO 104
<211> LENGTH: 19
<212> TYPE: DNA
<213> ORGANISM: Artificial Sequence
<220> FEATURE:
<223> OTHER INFORMATION: PCR primer-probe

<400> SEQUENCE: 104
ggctagtggg cgcatgtag                                                   19

<210> SEQ ID NO 105
<211> LENGTH: 19
<212> TYPE: DNA
<213> ORGANISM: Artificial Sequence
<220> FEATURE:
<223> OTHER INFORMATION: PCR primer-probe
```

<400> SEQUENCE: 105
ctggagatgc tggacgccc                                              19

<210> SEQ ID NO 106
<211> LENGTH: 20
<212> TYPE: DNA
<213> ORGANISM: Artificial Sequence
<220> FEATURE:
<223> OTHER INFORMATION: PCR primer-probe

<400> SEQUENCE: 106
cacgggacat tcaccacatc                                             20

<210> SEQ ID NO 107
<211> LENGTH: 19
<212> TYPE: DNA
<213> ORGANISM: Artificial Sequence
<220> FEATURE:
<223> OTHER INFORMATION: PCR primer-probe

<400> SEQUENCE: 107
gggtgccatc cacttcaca                                              19

<210> SEQ ID NO 108
<211> LENGTH: 27
<212> TYPE: DNA
<213> ORGANISM: Artificial Sequence
<220> FEATURE:
<223> OTHER INFORMATION: PCR primer-probe

<400> SEQUENCE: 108
ataaaaagac aaccaacggc cgactgc                                     27

<210> SEQ ID NO 109
<211> LENGTH: 19
<212> TYPE: DNA
<213> ORGANISM: Artificial Sequence
<220> FEATURE:
<223> OTHER INFORMATION: PCR primer-probe

<400> SEQUENCE: 109
ccaccccgag caaatctgt                                              19

<210> SEQ ID NO 110
<211> LENGTH: 22
<212> TYPE: DNA
<213> ORGANISM: Artificial Sequence
<220> FEATURE:
<223> OTHER INFORMATION: PCR primer-probe

<400> SEQUENCE: 110
aaatccagtc ccctactttt gg                                          22

<210> SEQ ID NO 111
<211> LENGTH: 23
<212> TYPE: DNA
<213> ORGANISM: Artificial Sequence
<220> FEATURE:
<223> OTHER INFORMATION: PCR primer-probe

<400> SEQUENCE: 111
cctgaatcct ggaggctcac gcc                                         23

<210> SEQ ID NO 112
<211> LENGTH: 20
<212> TYPE: DNA
<213> ORGANISM: Artificial Sequence
<220> FEATURE:
<223> OTHER INFORMATION: PCR primer-probe

<400> SEQUENCE: 112
ccatctgcat ccatcttgtt                                        20

<210> SEQ ID NO 113
<211> LENGTH: 20
<212> TYPE: DNA
<213> ORGANISM: Artificial Sequence
<220> FEATURE:
<223> OTHER INFORMATION: PCR primer-probe

<400> SEQUENCE: 113
ggccaccagg gtattatctg                                        20

<210> SEQ ID NO 114
<211> LENGTH: 23
<212> TYPE: DNA
<213> ORGANISM: Artificial Sequence
<220> FEATURE:
<223> OTHER INFORMATION: PCR primer-probe

<400> SEQUENCE: 114 ctcccccaccc ttgagaagtg cct                                   23

<210> SEQ ID NO 115
<211> LENGTH: 20
<212> TYPE: DNA
<213> ORGANISM: Artificial Sequence
<220> FEATURE:
<223> OTHER INFORMATION: PCR primer-probe

<400> SEQUENCE: 115
ggcccagctt gaatttttca                                        20

<210> SEQ ID NO 116
<211> LENGTH: 27
<212> TYPE: DNA
<213> ORGANISM: Artificial Sequence
<220> FEATURE:
<223> OTHER INFORMATION: PCR primer-probe

<400> SEQUENCE: 116
aagctatgag gaaagaagt acacgat                                 27

<210> SEQ ID NO 117
<211> LENGTH: 30
<212> TYPE: DNA
<213> ORGANISM: Artificial Sequence
<220> FEATURE:
<223> OTHER INFORMATION: PCR primer-probe

<400> SEQUENCE: 117
tcagccactg gcttctgtca taatcaggag                             30

<210> SEQ ID NO 118
<211> LENGTH: 21
<212> TYPE: DNA
<213> ORGANISM: Artificial Sequence
<220> FEATURE:
<223> OTHER INFORMATION: PCR primer-probe

```
<400> SEQUENCE: 118
caatgccatc ttgcgctaca t                                          21

<210> SEQ ID NO 119
<211> LENGTH: 25
<212> TYPE: DNA
<213> ORGANISM: Artificial Sequence
<220> FEATURE:
<223> OTHER INFORMATION: PCR primer-probe

<400> SEQUENCE: 119
gtccactcga atcttttctt cttca                                      25

<210> SEQ ID NO 120
<211> LENGTH: 27
<212> TYPE: DNA
<213> ORGANISM: Artificial Sequence
<220> FEATURE:
<223> OTHER INFORMATION: PCR primer-probe

<400> SEQUENCE: 120
ctcgcaagca caacatgtgt ggtgaga                                    27

<210> SEQ ID NO 121
<211> LENGTH: 20
<212> TYPE: DNA
<213> ORGANISM: Artificial Sequence
<220> FEATURE:
<223> OTHER INFORMATION: PCR primer-probe

<400> SEQUENCE: 121
cggtgtgaga agtgcagcaa                                            20

<210> SEQ ID NO 122
<211> LENGTH: 19
<212> TYPE: DNA
<213> ORGANISM: Artificial Sequence
<220> FEATURE:
<223> OTHER INFORMATION: PCR primer-probe

<400> SEQUENCE: 122
cctctcgcaa gtgctccat                                             19

<210> SEQ ID NO 123
<211> LENGTH: 24
<212> TYPE: DNA
<213> ORGANISM: Artificial Sequence
<220> FEATURE:
<223> OTHER INFORMATION: PCR primer-probe

<400> SEQUENCE: 123
ccagaccata gcacactcgg gcac                                       24

<210> SEQ ID NO 124
<211> LENGTH: 19
<212> TYPE: DNA
<213> ORGANISM: Artificial Sequence
<220> FEATURE:
<223> OTHER INFORMATION: PCR primer-probe

<400> SEQUENCE: 124
caagggagcg accaactga                                             19
```

<210> SEQ ID NO 125
<211> LENGTH: 28
<212> TYPE: DNA
<213> ORGANISM: Artificial Sequence
<220> FEATURE:
<223> OTHER INFORMATION: PCR primer-probe

<400> SEQUENCE: 125
gtttgccaag ttaaatttgg tacataat                          28

<210> SEQ ID NO 126
<211> LENGTH: 28
<212> TYPE: DNA
<213> ORGANISM: Artificial Sequence
<220> FEATURE:
<223> OTHER INFORMATION: PCR primer-probe

<400> SEQUENCE: 126
ctccatatcc aaacaaagca tgtgtgcg                          28

<210> SEQ ID NO 127
<211> LENGTH: 19
<212> TYPE: DNA
<213> ORGANISM: Artificial Sequence
<220> FEATURE:
<223> OTHER INFORMATION: PCR primer-probe

<400> SEQUENCE: 127
agaaccgcaa ggtgagcaa                                    19

<210> SEQ ID NO 128
<211> LENGTH: 21
<212> TYPE: DNA
<213> ORGANISM: Artificial Sequence
<220> FEATURE:
<223> OTHER INFORMATION: PCR primer-probe

<400> SEQUENCE: 128
tccaactgaa ggtccctgat g                                 21

<210> SEQ ID NO 129
<211> LENGTH: 26
<212> TYPE: DNA
<213> ORGANISM: Artificial Sequence
<220> FEATURE:
<223> OTHER INFORMATION: PCR primer-probe

<400> SEQUENCE: 129
tggagattct ccagcacgtc atcgac                            26

<210> SEQ ID NO 130
<211> LENGTH: 21
<212> TYPE: DNA
<213> ORGANISM: Artificial Sequence
<220> FEATURE:
<223> OTHER INFORMATION: PCR primer-probe

<400> SEQUENCE: 130
gcatggtagc cgaagatttc a                                 21

<210> SEQ ID NO 131
<211> LENGTH: 30
<212> TYPE: DNA
<213> ORGANISM: Artificial Sequence
<220> FEATURE:
<223> OTHER INFORMATION: PCR primer-probe

```
<400> SEQUENCE: 131
tttccggtaa tagtctgtct catagatatc                                      30

<210> SEQ ID NO 132
<211> LENGTH: 28
<212> TYPE: DNA
<213> ORGANISM: Artificial Sequence
<220> FEATURE:
<223> OTHER INFORMATION: PCR primer-probe

<400> SEQUENCE: 132
cgcgtcatac caaatctcc gattttga                                         28

<210> SEQ ID NO 133
<211> LENGTH: 22
<212> TYPE: DNA
<213> ORGANISM: Artificial Sequence
<220> FEATURE:
<223> OTHER INFORMATION: PCR primer-probe

<400> SEQUENCE: 133
gatatgattg gtcgctgctt tg                                              22

<210> SEQ ID NO 134
<211> LENGTH: 21
<212> TYPE: DNA
<213> ORGANISM: Artificial Sequence
<220> FEATURE:
<223> OTHER INFORMATION: PCR primer-probe

<400> SEQUENCE: 134
agaacttcca ttccccacca t                                               21

<210> SEQ ID NO 135
<211> LENGTH: 21
<212> TYPE: DNA
<213> ORGANISM: Artificial Sequence
<220> FEATURE:
<223> OTHER INFORMATION: PCR primer-probe

<400> SEQUENCE: 135
cagccaggac ctggccatcc g                                               21

<210> SEQ ID NO 136
<211> LENGTH: 19
<212> TYPE: DNA
<213> ORGANISM: Artificial Sequence
<220> FEATURE:
<223> OTHER INFORMATION: PCR primer-probe

<400> SEQUENCE: 136
cggactttgg gtgcgactt                                                  19

<210> SEQ ID NO 137
<211> LENGTH: 24
<212> TYPE: DNA
<213> ORGANISM: Artificial Sequence
<220> FEATURE:
<223> OTHER INFORMATION: PCR primer-probe

<400> SEQUENCE: 137
ttacaactct tccactggga cgat                                            24
```

<210> SEQ ID NO 138
<211> LENGTH: 23
<212> TYPE: DNA
<213> ORGANISM: Artificial Sequence
<220> FEATURE:
<223> OTHER INFORMATION: PCR primer-probe

<400> SEQUENCE: 138
ccacttgtcg aaccaccgct cgt                                              23

<210> SEQ ID NO 139
<211> LENGTH: 18
<212> TYPE: DNA
<213> ORGANISM: Artificial Sequence
<220> FEATURE:
<223> OTHER INFORMATION: PCR primer-probe

<400> SEQUENCE: 139
gcccagaggc tccatcgt                                                    18

<210> SEQ ID NO 140
<211> LENGTH: 23
<212> TYPE: DNA
<213> ORGANISM: Artificial Sequence
<220> FEATURE:
<223> OTHER INFORMATION: PCR primer-probe

<400> SEQUENCE: 140
cagaggtttg aacagtgcag aca                                              23

<210> SEQ ID NO 141
<211> LENGTH: 23
<212> TYPE: DNA
<213> ORGANISM: Artificial Sequence
<220> FEATURE:
<223> OTHER INFORMATION: PCR primer-probe

<400> SEQUENCE: 141
cctcttcctc cccagtcggc tga                                              23

<210> SEQ ID NO 142
<211> LENGTH: 20
<212> TYPE: DNA
<213> ORGANISM: Artificial Sequence
<220> FEATURE:
<223> OTHER INFORMATION: PCR primer-probe

<400> SEQUENCE: 142
ccacctcgcc atgattttc                                                   20

<210> SEQ ID NO 143
<211> LENGTH: 25
<212> TYPE: DNA
<213> ORGANISM: Artificial Sequence
<220> FEATURE:
<223> OTHER INFORMATION: PCR primer-probe

<400> SEQUENCE: 143
gcaatctctt caaacacttc atcct                                            25

<210> SEQ ID NO 144
<211> LENGTH: 25
<212> TYPE: DNA
<213> ORGANISM: Artificial Sequence
<220> FEATURE:
<223> OTHER INFORMATION: PCR primer-probe

```
<400> SEQUENCE: 144
tttgaccggg tattcccacc aggaa                                    25

<210> SEQ ID NO 145
<211> LENGTH: 20
<212> TYPE: DNA
<213> ORGANISM: Artificial Sequence
<220> FEATURE:
<223> OTHER INFORMATION: PCR primer-probe

<400> SEQUENCE: 145
tcagtggaga aggagttgga                                          20

<210> SEQ ID NO 146
<211> LENGTH: 20
<212> TYPE: DNA
<213> ORGANISM: Artificial Sequence
<220> FEATURE:
<223> OTHER INFORMATION: PCR primer-probe

<400> SEQUENCE: 146
tgccatatcc agaggaaaca                                          20

<210> SEQ ID NO 147
<211> LENGTH: 28
<212> TYPE: DNA
<213> ORGANISM: Artificial Sequence
<220> FEATURE:
<223> OTHER INFORMATION: PCR primer-probe

<400> SEQUENCE: 147
ccagtcaaca tctctgttgt cacaagca                                 28

<210> SEQ ID NO 148
<211> LENGTH: 19
<212> TYPE: DNA
<213> ORGANISM: Artificial Sequence
<220> FEATURE:
<223> OTHER INFORMATION: PCR primer-probe

<400> SEQUENCE: 148
tgcaaacgct ggtgtcaca                                           19

<210> SEQ ID NO 149
<211> LENGTH: 21
<212> TYPE: DNA
<213> ORGANISM: Artificial Sequence
<220> FEATURE:
<223> OTHER INFORMATION: PCR primer-probe

<400> SEQUENCE: 149
ccccacgagt tctggttctt c                                        21

<210> SEQ ID NO 150
<211> LENGTH: 22
<212> TYPE: DNA
<213> ORGANISM: Artificial Sequence
<220> FEATURE:
<223> OTHER INFORMATION: PCR primer-probe

<400> SEQUENCE: 150
cagcccccca actgacctca tc                                       22
```

```
<210> SEQ ID NO 151
<211> LENGTH: 21
<212> TYPE: DNA
<213> ORGANISM: Artificial Sequence
<220> FEATURE:
<223> OTHER INFORMATION: PCR primer-probe

<400> SEQUENCE: 151
gacttttgcc cgctaccttt c                                        21

<210> SEQ ID NO 152
<211> LENGTH: 26
<212> TYPE: DNA
<213> ORGANISM: Artificial Sequence
<220> FEATURE:
<223> OTHER INFORMATION: PCR primer-probe

<400> SEQUENCE: 152
gccactaact gcttcagtat gaagag                                   26

<210> SEQ ID NO 153
<211> LENGTH: 24
<212> TYPE: DNA
<213> ORGANISM: Artificial Sequence
<220> FEATURE:
<223> OTHER INFORMATION: PCR primer-probe

<400> SEQUENCE: 153
acagctcatt gttgtcacgc cgga                                     24

<210> SEQ ID NO 154
<211> LENGTH: 24
<212> TYPE: DNA
<213> ORGANISM: Artificial Sequence
<220> FEATURE:
<223> OTHER INFORMATION: PCR primer-probe

<400> SEQUENCE: 154
tgatggtcct atgtgtcaca ttca                                     24

<210> SEQ ID NO 155
<211> LENGTH: 20
<212> TYPE: DNA
<213> ORGANISM: Artificial Sequence
<220> FEATURE:
<223> OTHER INFORMATION: PCR primer-probe

<400> SEQUENCE: 155
tgggacagga aacacaccaa                                          20

<210> SEQ ID NO 156
<211> LENGTH: 30
<212> TYPE: DNA
<213> ORGANISM: Artificial Sequence
<220> FEATURE:
<223> OTHER INFORMATION: PCR primer-probe

<400> SEQUENCE: 156
caggtttcat accaacacag gcttcagcac                               30

<210> SEQ ID NO 157
<211> LENGTH: 18
<212> TYPE: DNA
<213> ORGANISM: Artificial Sequence
<220> FEATURE:
<223> OTHER INFORMATION: PCR primer-probe
```

```
<400> SEQUENCE: 157
aacccggcga tcgaaaag                                                 18

<210> SEQ ID NO 158
<211> LENGTH: 18
<212> TYPE: DNA
<213> ORGANISM: Artificial Sequence
<220> FEATURE:
<223> OTHER INFORMATION: PCR primer-probe

<400> SEQUENCE: 158
gggcctgctg tcctgaga                                                 18

<210> SEQ ID NO 159
<211> LENGTH: 24
<212> TYPE: DNA
<213> ORGANISM: Artificial Sequence
<220> FEATURE:
<223> OTHER INFORMATION: PCR primer-probe

<400> SEQUENCE: 159
tcttaggaac gccgtaccag ccgc                                          24

<210> SEQ ID NO 160
<211> LENGTH: 19
<212> TYPE: DNA
<213> ORGANISM: Artificial Sequence
<220> FEATURE:
<223> OTHER INFORMATION: PCR primer-probe

<400> SEQUENCE: 160
ccaacgcttg ccaaatcct                                                19

<210> SEQ ID NO 161
<211> LENGTH: 24
<212> TYPE: DNA
<213> ORGANISM: Artificial Sequence
<220> FEATURE:
<223> OTHER INFORMATION: PCR primer-probe

<400> SEQUENCE: 161
acggtagtga cagcatcaaa actc                                          24

<210> SEQ ID NO 162
<211> LENGTH: 24
<212> TYPE: DNA
<213> ORGANISM: Artificial Sequence
<220> FEATURE:
<223> OTHER INFORMATION: PCR primer-probe

<400> SEQUENCE: 162
aaccagctct ctgtgacccc aatt                                          24

<210> SEQ ID NO 163
<211> LENGTH: 20
<212> TYPE: DNA
<213> ORGANISM: Artificial Sequence
<220> FEATURE:
<223> OTHER INFORMATION: PCR primer-probe

<400> SEQUENCE: 163
gagaaccaat ctcaccgaca                                               20
```

```
<210> SEQ ID NO 164
<211> LENGTH: 20
<212> TYPE: DNA
<213> ORGANISM: Artificial Sequence
<220> FEATURE:
<223> OTHER INFORMATION: PCR primer-probe

<400> SEQUENCE: 164
cacccgagtg taaccatagc                                               20

<210> SEQ ID NO 165
<211> LENGTH: 24
<212> TYPE: DNA
<213> ORGANISM: Artificial Sequence
<220> FEATURE:
<223> OTHER INFORMATION: PCR primer-probe

<400> SEQUENCE: 165
acaggtattc ctctgccagc tgcc                                          24

<210> SEQ ID NO 166
<211> LENGTH: 18
<212> TYPE: DNA
<213> ORGANISM: Artificial Sequence
<220> FEATURE:
<223> OTHER INFORMATION: PCR primer-probe

<400> SEQUENCE: 166
gccgagatcg ccaagatg                                                 18

<210> SEQ ID NO 167
<211> LENGTH: 27
<212> TYPE: DNA
<213> ORGANISM: Artificial Sequence
<220> FEATURE:
<223> OTHER INFORMATION: PCR primer-probe

<400> SEQUENCE: 167
cttttgatgg tagagttcca gtgattc                                       27

<210> SEQ ID NO 168
<211> LENGTH: 24
<212> TYPE: DNA
<213> ORGANISM: Artificial Sequence
<220> FEATURE:
<223> OTHER INFORMATION: PCR primer-probe

<400> SEQUENCE: 168
cagcattgtc tgtcctccct ggca                                          24

<210> SEQ ID NO 169
<211> LENGTH: 18
<212> TYPE: DNA
<213> ORGANISM: Artificial Sequence
<220> FEATURE:
<223> OTHER INFORMATION: PCR primer-probe

<400> SEQUENCE: 169
gtgaggcagc gcgactct                                                 18

<210> SEQ ID NO 170
<211> LENGTH: 23
<212> TYPE: DNA
<213> ORGANISM: Artificial Sequence
<220> FEATURE:
<223> OTHER INFORMATION: PCR primer-probe
```

-continued

```
<400> SEQUENCE: 170
tgccaatggt gtacaacact tca                                          23

<210> SEQ ID NO 171
<211> LENGTH: 21
<212> TYPE: DNA
<213> ORGANISM: Artificial Sequence
<220> FEATURE:
<223> OTHER INFORMATION: PCR primer-probe

<400> SEQUENCE: 171
tgccttcccg ggctgaggac t                                            21

<210> SEQ ID NO 172
<211> LENGTH: 19
<212> TYPE: DNA
<213> ORGANISM: Artificial Sequence
<220> FEATURE:
<223> OTHER INFORMATION: PCR primer-probe

<400> SEQUENCE: 172
ccaaccctgc agactccaa                                               19

<210> SEQ ID NO 173
<211> LENGTH: 28
<212> TYPE: DNA
<213> ORGANISM: Artificial Sequence
<220> FEATURE:
<223> OTHER INFORMATION: PCR primer-probe

<400> SEQUENCE: 173
atgtataatg ttcctgccaa cttgtatg                                     28

<210> SEQ ID NO 174
<211> LENGTH: 25
<212> TYPE: DNA
<213> ORGANISM: Artificial Sequence
<220> FEATURE:
<223> OTHER INFORMATION: PCR primer-probe

<400> SEQUENCE: 174
cctgggacca tccgtggaga cttct                                        25

<210> SEQ ID NO 175
<211> LENGTH: 20
<212> TYPE: DNA
<213> ORGANISM: Artificial Sequence
<220> FEATURE:
<223> OTHER INFORMATION: PCR primer-probe

<400> SEQUENCE: 175
ggctgtggct gaggctgtag                                              20

<210> SEQ ID NO 176
<211> LENGTH: 21
<212> TYPE: DNA
<213> ORGANISM: Artificial Sequence
<220> FEATURE:
<223> OTHER INFORMATION: PCR primer-probe

<400> SEQUENCE: 176
ggagcattcg aggtcaaatc a                                            21
```

<210> SEQ ID NO 177
<211> LENGTH: 28
<212> TYPE: DNA
<213> ORGANISM: Artificial Sequence
<220> FEATURE:
<223> OTHER INFORMATION: PCR primer-probe

<400> SEQUENCE: 177
ttcccagagt gtctcacctc cagcagag                              28

<210> SEQ ID NO 178
<211> LENGTH: 22
<212> TYPE: DNA
<213> ORGANISM: Artificial Sequence
<220> FEATURE:
<223> OTHER INFORMATION: PCR primer-probe

<400> SEQUENCE: 178
gaaggtgttg gaggcactca ag                                    22

<210> SEQ ID NO 179
<211> LENGTH: 21
<212> TYPE: DNA
<213> ORGANISM: Artificial Sequence
<220> FEATURE:
<223> OTHER INFORMATION: PCR primer-probe

<400> SEQUENCE: 179
ggtttacacc gctggagcta a                                     21

<210> SEQ ID NO 180
<211> LENGTH: 24
<212> TYPE: DNA
<213> ORGANISM: Artificial Sequence
<220> FEATURE:
<223> OTHER INFORMATION: PCR primer-probe

<400> SEQUENCE: 180
atcccagcag gcctcgttga tgag                                  24

<210> SEQ ID NO 181
<211> LENGTH: 20
<212> TYPE: DNA
<213> ORGANISM: Artificial Sequence
<220> FEATURE:
<223> OTHER INFORMATION: PCR primer-probe

<400> SEQUENCE: 181
gcatcaggct gtcattatgg                                       20

<210> SEQ ID NO 182
<211> LENGTH: 20
<212> TYPE: DNA
<213> ORGANISM: Artificial Sequence
<220> FEATURE:
<223> OTHER INFORMATION: PCR primer-probe

<400> SEQUENCE: 182
agtagttgtg ctgcccttcc                                       20

<210> SEQ ID NO 183
<211> LENGTH: 28
<212> TYPE: DNA
<213> ORGANISM: Artificial Sequence
<220> FEATURE:
<223> OTHER INFORMATION: PCR primer-probe

```
<400> SEQUENCE: 183
tgtccttacc tgtgggagct gtaaggtc                                      28

<210> SEQ ID NO 184
<211> LENGTH: 21
<212> TYPE: DNA
<213> ORGANISM: Artificial Sequence
<220> FEATURE:
<223> OTHER INFORMATION: PCR primer-probe

<400> SEQUENCE: 184
gggacggtgt tcacattcaa g                                             21

<210> SEQ ID NO 185
<211> LENGTH: 23
<212> TYPE: DNA
<213> ORGANISM: Artificial Sequence
<220> FEATURE:
<223> OTHER INFORMATION: PCR primer-probe

<400> SEQUENCE: 185
caggatccca gaagtcaatg ttg                                           23

<210> SEQ ID NO 186
<211> LENGTH: 24
<212> TYPE: DNA
<213> ORGANISM: Artificial Sequence
<220> FEATURE:
<223> OTHER INFORMATION: PCR primer-probe

<400> SEQUENCE: 186
tcgccagtct cccaactatc gcgt                                          24

<210> SEQ ID NO 187
<211> LENGTH: 28
<212> TYPE: DNA
<213> ORGANISM: Artificial Sequence
<220> FEATURE:
<223> OTHER INFORMATION: PCR primer-probe

<400> SEQUENCE: 187
ggctactctg atctatgttg ataaggaa                                      28

<210> SEQ ID NO 188
<211> LENGTH: 20
<212> TYPE: DNA
<213> ORGANISM: Artificial Sequence
<220> FEATURE:
<223> OTHER INFORMATION: PCR primer-probe

<400> SEQUENCE: 188
gcttcagccc atccttagca                                               20

<210> SEQ ID NO 189
<211> LENGTH: 22
<212> TYPE: DNA
<213> ORGANISM: Artificial Sequence
<220> FEATURE:
<223> OTHER INFORMATION: PCR primer-probe

<400> SEQUENCE: 189
cacacgggtg cctggttctc ca                                            22
```

<210> SEQ ID NO 190
<211> LENGTH: 24
<212> TYPE: DNA
<213> ORGANISM: Artificial Sequence
<220> FEATURE:
<223> OTHER INFORMATION: PCR primer-probe

<400> SEQUENCE: 190
ccattctatc atcaacgggt acaa                                         24

<210> SEQ ID NO 191
<211> LENGTH: 23
<212> TYPE: DNA
<213> ORGANISM: Artificial Sequence
<220> FEATURE:
<223> OTHER INFORMATION: PCR primer-probe

<400> SEQUENCE: 191
tcagcaagtg ggaaggtgta atc                                          23

<210> SEQ ID NO 192
<211> LENGTH: 25
<212> TYPE: DNA
<213> ORGANISM: Artificial Sequence
<220> FEATURE:
<223> OTHER INFORMATION: PCR primer-probe

<400> SEQUENCE: 192
tctccacaga caaggccagg actcg                                        25

<210> SEQ ID NO 193
<211> LENGTH: 20
<212> TYPE: DNA
<213> ORGANISM: Artificial Sequence
<220> FEATURE:
<223> OTHER INFORMATION: PCR primer-probe

<400> SEQUENCE: 193
ggctggtcgg cagagagtag                                              20

<210> SEQ ID NO 194
<211> LENGTH: 21
<212> TYPE: DNA
<213> ORGANISM: Artificial Sequence
<220> FEATURE:
<223> OTHER INFORMATION: PCR primer-probe

<400> SEQUENCE: 194
tgaggaaagg tttgggattg a                                            21

<210> SEQ ID NO 195
<211> LENGTH: 29
<212> TYPE: DNA
<213> ORGANISM: Artificial Sequence
<220> FEATURE:
<223> OTHER INFORMATION: PCR primer-probe

<400> SEQUENCE: 195
aaactcatgt aaaccacggc cgaatgttg                                    29

<210> SEQ ID NO 196
<211> LENGTH: 20
<212> TYPE: DNA
<213> ORGANISM: Artificial Sequence
<220> FEATURE:
<223> OTHER INFORMATION: PCR primer-probe

<400> SEQUENCE: 196
cctgaacatg aaggagctga                                              20

<210> SEQ ID NO 197
<211> LENGTH: 19
<212> TYPE: DNA
<213> ORGANISM: Artificial Sequence
<220> FEATURE:
<223> OTHER INFORMATION: PCR primer-probe

<400> SEQUENCE: 197
catcacgtct ccgaactcc                                               19

<210> SEQ ID NO 198
<211> LENGTH: 21
<212> TYPE: DNA
<213> ORGANISM: Artificial Sequence
<220> FEATURE:
<223> OTHER INFORMATION: PCR primer-probe

<400> SEQUENCE: 198
tcccgatggt ctgcagcagc t                                            21

<210> SEQ ID NO 199
<211> LENGTH: 20
<212> TYPE: DNA
<213> ORGANISM: Artificial Sequence
<220> FEATURE:
<223> OTHER INFORMATION: PCR primer-probe

<400> SEQUENCE: 199
catcttccag gaggaccact                                              20

<210> SEQ ID NO 200
<211> LENGTH: 20
<212> TYPE: DNA
<213> ORGANISM: Artificial Sequence
<220> FEATURE:
<223> OTHER INFORMATION: PCR primer-probe

<400> SEQUENCE: 200
tccgaccttc aatcatttca                                              20

<210> SEQ ID NO 201
<211> LENGTH: 24
<212> TYPE: DNA
<213> ORGANISM: Artificial Sequence
<220> FEATURE:
<223> OTHER INFORMATION: PCR primer-probe

<400> SEQUENCE: 201
ctctgtggca ccctggacta cctg                                         24

<210> SEQ ID NO 202
<211> LENGTH: 20
<212> TYPE: DNA
<213> ORGANISM: Artificial Sequence
<220> FEATURE:
<223> OTHER INFORMATION: PCR primer-probe

<400> SEQUENCE: 202
cctggaggct gcaacatacc                                              20

```
<210> SEQ ID NO 203
<211> LENGTH: 23
<212> TYPE: DNA
<213> ORGANISM: Artificial Sequence
<220> FEATURE:
<223> OTHER INFORMATION: PCR primer-probe

<400> SEQUENCE: 203
tacaatggct ttggaggata gca                                          23

<210> SEQ ID NO 204
<211> LENGTH: 25
<212> TYPE: DNA
<213> ORGANISM: Artificial Sequence
<220> FEATURE:
<223> OTHER INFORMATION: PCR primer-probe

<400> SEQUENCE: 204
atcctcctga agccttttc gcagc                                         25

<210> SEQ ID NO 205
<211> LENGTH: 20
<212> TYPE: DNA
<213> ORGANISM: Artificial Sequence
<220> FEATURE:
<223> OTHER INFORMATION: PCR primer-probe

<400> SEQUENCE: 205
tgttttgatt cccgggctta                                              20

<210> SEQ ID NO 206
<211> LENGTH: 24
<212> TYPE: DNA
<213> ORGANISM: Artificial Sequence
<220> FEATURE:
<223> OTHER INFORMATION: PCR primer-probe

<400> SEQUENCE: 206
caaagctgtc agctctagca aaag                                         24

<210> SEQ ID NO 207
<211> LENGTH: 28
<212> TYPE: DNA
<213> ORGANISM: Artificial Sequence
<220> FEATURE:
<223> OTHER INFORMATION: PCR primer-probe

<400> SEQUENCE: 207
tgccttcttc ctccctcact tctcacct                                     28

<210> SEQ ID NO 208
<211> LENGTH: 20
<212> TYPE: DNA
<213> ORGANISM: Artificial Sequence
<220> FEATURE:
<223> OTHER INFORMATION: PCR primer-probe

<400> SEQUENCE: 208
gccaactgct ttcatttgtg                                              20

<210> SEQ ID NO 209
<211> LENGTH: 20
<212> TYPE: DNA
<213> ORGANISM: Artificial Sequence
<220> FEATURE:
<223> OTHER INFORMATION: PCR primer-probe
```

```
<400> SEQUENCE: 209
actcaggccc atttccttta                                            20

<210> SEQ ID NO 210
<211> LENGTH: 28
<212> TYPE: DNA
<213> ORGANISM: Artificial Sequence
<220> FEATURE:
<223> OTHER INFORMATION: PCR primer-probe

<400> SEQUENCE: 210
agggatctga accaatacag agcagaca                                   28

<210> SEQ ID NO 211
<211> LENGTH: 20
<212> TYPE: DNA
<213> ORGANISM: Artificial Sequence
<220> FEATURE:
<223> OTHER INFORMATION: PCR primer-probe

<400> SEQUENCE: 211
aatccaaggg ggagagtgat                                            20

<210> SEQ ID NO 212
<211> LENGTH: 20
<212> TYPE: DNA
<213> ORGANISM: Artificial Sequence
<220> FEATURE:
<223> OTHER INFORMATION: PCR primer-probe

<400> SEQUENCE: 212
gtacagattt tgcccgagga                                            20

<210> SEQ ID NO 213
<211> LENGTH: 26
<212> TYPE: DNA
<213> ORGANISM: Artificial Sequence
<220> FEATURE:
<223> OTHER INFORMATION: PCR primer-probe

<400> SEQUENCE: 213
catatggact ttgactcagc tgtggc                                     26

<210> SEQ ID NO 214
<211> LENGTH: 18
<212> TYPE: DNA
<213> ORGANISM: Artificial Sequence
<220> FEATURE:
<223> OTHER INFORMATION: PCR primer-probe

<400> SEQUENCE: 214
gcctcggtgt gcctttca                                              18

<210> SEQ ID NO 215
<211> LENGTH: 19
<212> TYPE: DNA
<213> ORGANISM: Artificial Sequence
<220> FEATURE:
<223> OTHER INFORMATION: PCR primer-probe

<400> SEQUENCE: 215
cgtgatgtgc gcaatcatg                                             19
```

-continued

```
<210> SEQ ID NO 216
<211> LENGTH: 22
<212> TYPE: DNA
<213> ORGANISM: Artificial Sequence
<220> FEATURE:
<223> OTHER INFORMATION: PCR primer-probe

<400> SEQUENCE: 216
catcgccagc tacgccctgc tc                                              22
```

PREDICTION OF LIKELIHOOD OF CANCER RECURRENCE

The present application claims the benefit under 35 U.S.C. 119(e) of the filing date of U.S. application Ser. No. 60/482,339, filed on Jun. 24, 2003.

BACKGROUND OF THE INVENTION

1. Field of the Invention

The present invention provides gene sets the expression of which is important in the diagnosis and/or prognosis of cancer.

2. Description of the Related Art

Oncologists have a number of treatment options available to them, including different combinations of chemotherapeutic drugs that are characterized as "standard of care," and a number of drugs that do not carry a label claim for particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

In the past few years, several groups have published studies concerning the classification of various cancer types by microarray gene expression analysis (see, e.g. Golub et al., *Science* 286:531–537 (1999); Bhattacharjae et al., *Proc. Natl. Acad. Sci. USA* 98:13790–13795 (2001); Chen-Hsiang et al., *Bioinformatics* 17 (Suppl. 1): S316–S322 (2001); Ramaswamy et al., *Proc. Natl. Acad. Sci. USA* 98:15149–15154 (2001)). Certain classifications of human breast cancers based on gene expression patterns have also been reported (Martin et al., *Cancer Res.* 60:2232–2238 (2000); West et al., *Proc. Natl. Acad. Sci. USA* 98:11462–11467 (2001); Sorlie et al., *Proc. Natl. Acad. Sci. USA* 98:10869–10874 (2001); Yan et al., *Cancer Res.* 61:8375–8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed hundreds of genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as ErbB2$^+$ subgroup, and subgroups characterized by low to absent gene expression of the estrogen receptor (ER) and a few additional transcriptional factors (Perou et al., *Nature* 406:747–752 (2000)) does not reflect the cellular and molecular heterogeneity of breast cancer, and does not allow the design of treatment strategies maximizing patient response.

In particular, once a patient is diagnosed with cancer, such as breast or ovarian cancer, there is a strong need for methods that allow the physician to predict the expected course of disease, including the likelihood of cancer recurrence, long-term survival of the patient, and the like, and select the most appropriate treatment option accordingly.

SUMMARY OF THE INVENTION

The present invention provides a set of genes, the expression of which has prognostic value, specifically with respect to disease-free survival.

The present invention accommodates the use of archived paraffin-embedded biopsy material for assay of all markers in the set, and therefore is compatible with the most widely available type of biopsy material. It is also compatible with several different methods of tumor tissue harvest, for example, via core biopsy or fine needle aspiration. Further, for each member of the gene set, the invention specifies oligonucleotide sequences that can be used in the test.

In one aspect, the present invention concerns a method of predicting the likelihood of long-term survival of a cancer patient without the recurrence of cancer, comprising determining the expression level of one or more prognostic RNA transcripts or their expression products in a cancer cell obtained from the patient, normalized against the expression level of all RNA transcripts or their products in said cancer cell, or of a reference set of RNA transcripts or their expression products, wherein the prognostic RNA transcript is the transcript of one or more genes selected from the group consisting of B_Catenin; BAG1; BIN1; BUB1; C20_orf1; CCNB1; CCNE2; CDC20; CDH1; CEGP1; CIAP1; cMYC; CTSL2; DKFZp586M07; DR5; EpCAM; EstR1; FOXM1; GRB7; GSTM1; GSTM3; HER2; HNRPAB; ID1; IGF1R; ITGA7; Ki_67; KNSL2; LMNB1; MCM2; MELK; MMP12; MMP9; MYBL2; NEK2; NME1; NPD009; PCNA; PR; PREP; PTTG1; RPLPO; Src; STK15; STMY3; SURV; TFRC; TOP2A; and TS;

wherein expression of one or more of BUB1; C20_orf1; CCNB1; CCNE2; CDC20; CDH1; CTSL2; EpCAM; FOXM1; GRB7; HER2; HNRPAB; Ki_67; KNSL2; LMNB1; MCM2; MELK; MMP12; MMP9; MYBL2; NEK2; NME1; PCNA; PREP; PTTG1; Src; STK15;

STMY3; SURV; TFRC; TOP2A; and TS indicates a decreased likelihood of long-term survival without cancer recurrence; and the expression of one or more of BAG1; BCatenin; BIN1; CEGP1; CIAP1; cMYC; DKFZp586M07; DR5; EstR1; GSTM1; GSTM3; ID1; IGF1R; ITGA7; NPD009; PR; and RPLPO indicates an increased likelihood of long-term survival without cancer recurrence.

In various embodiments, the expression level of at least 2, or at least 5, or at least 10, or at least 15, or at least 20, or a least 25 prognostic RNA transcripts or their expression products is determined.

In another embodiment, the cancer is breast cancer or ovarian cancer.

In yet another embodiment, the cancer is node negative, ER positive breast cancer.

In a further embodiment, the RNA comprises intronic RNA.

In a still further embodiment, the expression level of one or more prognostic RNA transcripts or their expression products of one or more genes selected from the group consisting of MMP9, GSTM1, MELK, PR, DKFZp586M07, GSTM3, CDC20, CCNB1, STMY3, GRB7, MYBL2, CEGP1, SURV, LMNB1, CTSL2, PTTG1, BAG1, KNSL2, CIAP1, PREP, NEK2, EpCAM, PCNA, C20_orf1, ITGA7, ID1 B_Catenin, EstR1, CDH1, TS HER2, and cMYC is determined, wherein expression of one or more of C20_orf1; CCNB1; CDC20; CDH1; CTSL2; EpCAM; GRB7; HER2; KNSL2; LMNB1; MCM2; MMP9; MYBL2; NEK2; PCNA; PREP; PTTG1; STMY3; SURV; TS; and MELK indicates a decreased likelihood of long-term survival without cancer recurrence; and the expression of one or more of BAG1; BCatenin; CEGP1; CIAP1; cMYC; DKFZp586M07; EstR1; GSTM1; GSTM3; ID1; ITGA7; and PR indicates an increased likelihood of long-term survival without cancer recurrence.

In another embodiment, the expression level of one or more prognostic RNA transcripts or their expression products of one or more genes selected from the group consisting of GRB7, SURV, PR, LMNB1, MYBL2, HER2, GSTM1, MELK, S20_orf1, PTTG1, BUB1, CDC20, CCNB1, STMY3, KNSL2, CTSL2, MCM2, NEK2, DR5, Ki_67, CCNE2, TOP2A, PCNA, PREP, FOXM1, NME1, CEGP1, BAG1, STK15, HNRPAB, EstR1, MMP9, DKFZp586M07, TS, Src, BIN1, NP009, RPLPO, GSTM3, MMP12, TFRC, and IGF1R is determined, wherein expression of one or more of GRB7; SURV; LMNB1; MYBL2; HER2; MELK; C20_orf1; PTTG1; BUB1; CDC20; CCNB1; STMY3; KNSL2; CTSL2; MCM2; NEK2; Ki_67; CCNE2; TOP2A_4; PCNA; PREP; FOXM1; NME1; STK15; HNRPAB; MMP9; TS; Src; MMP12; and TFRC indicates a decreased likelihood of long-term survival without cancer recurrence; and the expression of one or more of PR; GSTM1; DR5; CEGP1; BAG1; EstR1; DKFZp586M07; BIN1; NPD009; RPLPO; GSTM3; IGF1R indicates an increased likelihood of long-term survival without cancer recurrence.

In another aspect, the invention concerns a method of predicting the likelihood of long-term survival of a cancer patient without the recurrence of cancer, comprising determining the expression level of one or more prognostic RNA transcripts or their expression products in a cancer cell obtained from said patient, normalized against the expression level of all RNA transcripts or their products in the cancer cell, or of a reference set of RNA transcripts or their expression products, wherein the prognostic RNA transcript is the transcript of one or more genes selected from the group consisting of GRB7; LMNB1; ER; STMY3; KLK10; PR; KRT5; FGFR1; MCM6; SNRPF, wherein expression of one or more of GRB7, LMNB1, STMY3, KLK10, FGFR1, and SNRPF indicates a decreased likelihood or long term survival without cancer recurrence; and the expression of one or more of ER, PR, KRT5 and MCM6 ER, PR, KRT5 and MCM6indicates an increased likelihood of long-term survival without cancer recurrence.

In an embodiment of this method, the RNA is isolated from a fixed, wax-embedded breast cancer tissue specimen of the patient.

In another embodiment, the RNA is isolated from core biopsy tissue or fine needle aspirate cells.

In a different aspect, the invention concerns an array comprising polynucleotides hybridizing to two or more of the following genes: B_Catenin; BAG1; BIN1; BUB1; C20_orf1; CCNB1; CCNE2; CDC20; CDH1; CEGP1; CIAP1; cMYC; CTSL2; DKFZp586M07; DR5; EpCAM; EstR1; FOXM1; GRB7; GSTM1; GSTM3; HER2; HNR-PAB; ID1; IGF1R; ITGA7; Ki_67; KNSL2; LMNB1; MCM2; MELK; MMP12; MMP9; MYBL2; NEK2; NME1; NPD009; PCNA; PR; PREP; PTTG1; RPLPO; Src; STK15; STMY3; SURV; TFRC; TOP2A; and TS, immobilized on a solid surface.

In an embodiment, the array comprises polynucleotides hybridizing to two or more of the following genes: MMP9, GSTM1, MELK, PR, DKFZp586M07, GSTM3, CDC20, CCNB1, STMY3, GRB7, MYBL2, CEGP1, SURV, LMNB1, CTSL2, PTTG1, BAG1, KNSL2, CIAP1, PREP, NEK2, EpCAM, PCNA, C20_orf1, ITGA7, ID1 B_Catenin, EstR1, CDH1, TS HER2, and cMYC.

In another embodiment, the array comprises polynucleotides hybridizing to two or more of the following genes: GRB7, SURV, PR, LMNB1, MYBL2, HER2, GSTM1, MELK, S20_orf1, PTTG1, BUB1, CDC20, CCNB1, STMY3, KNSL2, CTSL2, MCM2, NEK2, DR5, Ki_67, CCNE2, TOP2A, PCNA, PREP, FOXM1, NME1, CEGP1, BAG1, STK15, HNRPAB, EstR1, MMP9, DKFZp586M07, TS, Src, BIN1, NP009, RPLPO, GSTM3, MMP12, TFRC, and IGF1R.

In a further embodiment, the arrays comprise polynucleotides hybridizing to at least 3, or at least 5, or at least 10, or at least 15, or at least 20, or at least 25 of the listed genes.

In a still further embodiment, the arrays comprise polynucleotides hybridizing to all of the listed genes.

In yet another embodiment, the arrays comprise more than one polynucleotide hybridizing to the same gene.

In an additional embodiment, the arrays comprise intron-based sequences.

In another embodiment, the polynucleotides are cDNAs, which can, for example, be about 500 to 5000 bases long.

In yet another embodiment, the polynucleotides are oligonucleotides, which can, for example, be about 20 to 80 bases long.

The arrays can, for example, be immobilized on glass, and can contain hundreds of thousand, e.g. 330,000 oligonucleotides.

In a further aspect, the invention concerns a method of predicting the likelihood of long-term survival of a patient diagnosed with invasive breast cancer, without the recurrence of breast cancer, comprising the steps of (a) determining the expression levels of the RNA transcripts or the expression products of genes of a gene set selected from the group consisting of B_Catenin; BAG1; BIN1; BUB1; C20_orf1; CCNB1; CCNE2; CDC20; CDH1; CEGP1; CIAP1; cMYC; CTSL2; DKFZp586M07; DR5; EpCAM; EstR1; FOXM1; GRB7; GSTM1; GSTM3; HER2; HNRPAB; ID1; IGF1R; ITGA7; Ki_67; KNSL2; LMNB1; MCM2; MELK; MMP12; MMP9; MYBL2; NEK2; NME1; NPD009; PCNA; PR; PREP; PTTG1; RPLPO; Src; STK15; STMY3; SURV; TFRC; TOP2A; and TS in a breast cancer cell obtained from the patient, normalized against the expression levels of all RNA transcripts or their expression products in said breast cancer cell, or of a reference set of RNA transcripts or their products;

(b) subjecting the data obtained in step (a) to statistical analysis; and;

(c) determining whether the likelihood of said long-term survival has increased or decreased.

In a still further aspect, the invention concerns a method of preparing a personalized genomics profile for a patient, comprising the steps of (a) subjecting RNA extracted from a breast tissue obtained from the patient to gene expression analysis;

(b) determining the expression level in the tissue of one or more genes selected from the breast cancer gene set listed in any one of Tables 1 and 2, wherein the expression level is normalized against a control gene or genes and optionally is compared to the amount found in a breast cancer reference tissue set; and (c) creating a report summarizing the data obtained by said gene expression analysis.

The breast tissue may comprise breast cancer cells.

In another embodiment, the breast tissue is obtained from a fixed, paraffin-embedded biopsy sample, in which the RNA may be fragmented.

The report may include prediction of the likelihood of long term survival of the patient and/or a recommendation for a treatment modality of said patient.

In a further aspect, the invention concerns a method for measuring levels of mRNA products of genes listed in Tables 1 and 2 by real time polymerase chain reaction (RT-PCR), by using an amplicon listed in Table 3 and a primer-probe set listed in Tables 4A–4D.

In a still further aspect, the invention concerns a PCR primer-probe set listed in Tables 4A–4D, and a PCR amplicon listed in Table 3.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The term "node negative" cancer, such as "node negative" breast cancer, is used herein to refer to cancer that has not spread to the lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

Methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization (Parker & Barnes, Methods in Molecular Biology 106: 247–283 (1999)); RNAse protection assays (Hod, Biotechniques 13:852–854 (1992)); and PCR-based methods, such as reverse transcription polymerase chain reaction (RT-PCR) (Weis et al., Trends in Genetics 8:263–264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. PCR-based Gene Expression Profiling Methods a. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986–994 (1996).

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84–91 [2000]; K. Specht et al., Am. J. Pathol. 158: 419–29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

b. MassARRAY System

In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100: 3059–3064 (2003).

c. Other PCR-Based Methods

Further PCR-based techniques include, for example, differential display (Liang and Pardee, Science 257:967–971 (1992)); amplified fragment length polymorphism (iAFLP) (Kawamoto et al., Genome Res. 12:1305–1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888–1898 (2001)); and high coverage expression profiling (HiCEP) analysis (Fukumura et al., Nucl. Acids. Res. 31(16) e94 (2003)).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106–149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10–14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484–487 (1995); and Velculescu et al., *Cell* 88:243–51 (1997).

5. Gene Expression Analysis by Massively Parallel Signature Sequencing (MPSS)

This method, described by Brenner et al., *Nature Biotechnology* 18:630–634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

6. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

7. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

8. General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al,. *J Molec. Diagnostics* 2: 84–91 [2000]; K. Specht et al., *Am. J. Pathol.* 158: 419–29 [2001]). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined, dependent on the predicted likelihood of cancer recurrence.

9. Breast Cancer Gene Set, Assayed Gene Subsequences, and Clinical Application of Gene Expression Data An important aspect of the present invention is to use the measured expression of certain genes by breast cancer tissue to provide prognostic information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) of tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

10. Design of Intron-Based PCR Primers and Probes

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res.* 12(4):656–64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365–386)

The most important factors considered in PCR primer design include primer length, melting temperature (Tm), and G/C content, specificity, complementary primer sequences, and 3'-end sequence. In general, optimal PCR primers are generally 17–30 bases in length, and contain about 20–80%, such as, for example, about 50–60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133–155; Innis and Gelfand, "Optimization of PCRs" in: *PCR Protocols, A Guide to Methods and Applications*, CRC Press, London, 1994, pp. 5–11; and Plasterer, T. N. Primerselect: Primer and probe design. *Methods Mol. Biol.* 70:520–527 (1997), the entire disclosures of which are hereby expressly incorporated by reference.

Further details of the invention will be described in the following non-limiting Example.

EXAMPLE

A Phase II Study of Gene Expression in 242 Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival.

Study Design

Molecular assays were performed on paraffin-embedded, formalin-fixed primary breast tumor tissues obtained from 252 individual patients diagnosed with invasive breast cancer. All patients were lymph node-negative, ER-positive, and treated with Tamoxifen. Mean age was 52 years, and mean clinical tumor size was 2 cm. Median follow-up was 10.9 years. As of Jan. 1, 2003, 41 patients had local or distant disease recurrence or breast cancer death. Patients were included in the study only if histopathologic assessment, performed as described in the Materials and Methods section, indicated adequate amounts of tumor tissue and homogeneous pathology.

Materials and Methods

Each representative tumor block was characterized by standard histopathology for diagnosis, semi-quantitative assessment of amount of tumor, and tumor grade. When tumor area was less than 70% of the section, the tumor area was grossly dissected and tissue was taken from 6 (10 micron) sections. Otherwise, a total of 3 sections (also 10 microns in thickness each) were prepared. Sections were placed in two Costar Brand Microcentrifuge Tubes (Polypropylene, 1.7 mL tubes, clear). If more than one tumor block was obtained as part of the surgical procedure, the block most representative of the pathology was used for analysis.

Gene Expression Analysis mRNA was extracted and purified from fixed, paraffin-embedded tissue samples, and prepared for gene expression analysis as described in chapter 6 above.

Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 187 cancer-related genes and 5 reference genes. Adequate RT-PCR profiles were obtained from 242 of the 252 patients. The threshold cycle (CT) values for each patient were normalized based on the median of the 7 reference genes for that particular patient. Clinical outcome data were available for all patients from a review of registry data and selected patient charts. Outcomes were classified as:

Event: Alive with local, regional or distant breast cancer recurrence or death due to breast cancer.

No Event: Alive without local, regional or distant breast cancer recurrence or alive with contralateral breast cancer recurrence or alive with non-breast second primary cancer or died prior to breast cancer recurrence.

Analysis was performed by:

A. determination of the relationship between normalized gene expression and the binary outcomes of 0 or 1;

B. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of Patients with Invasive Breast Carcinoma by Binary Approach

In the first (binary) approach, analysis was performed on all 242 patients with invasive breast carcinoma. A t test was performed on the groups of patients classified as either no recurrence and no breast cancer related death at 10 years, versus recurrence, or breast cancer-related death at 10 years, and the p-values for the differences between the groups for each gene were calculated.

Table 1 lists the 33 genes for which the p-value for the differences between the groups was <0.05. The first column of mean expression values pertains to patients who had a metastatic recurrence of nor died from breast cancer. The second column of mean expression values pertains to patients who neither had a metastatic recurrence of nor died from breast cancer.

TABLE 1

| Gene | Mean group A Event | Mean group B No event | T statistic | P value |
|---|---|---|---|---|
| MMP9 | −3.15 | −4.27 | 3.75 | 0.00 |
| GSTM1 | −5.02 | −4.03 | −3.56 | 0.00 |
| MELK | −3.89 | −4.66 | 3.34 | 0.00 |
| PR | −4.56 | −3.18 | −3.27 | 0.00 |
| DKFZp586M07 | −3.83 | −2.94 | −3.09 | 0.00 |
| GSTM3 | −2.56 | −1.69 | −3.06 | 0.00 |
| MCM2 | −3.51 | −4.08 | 3.03 | 0.00 |
| CDC20 | −3.01 | −3.75 | 3.01 | 0.00 |
| CCNB1 | −4.48 | −5.17 | 3.02 | 0.00 |
| STMY3 | −0.58 | −1.20 | 2.95 | 0.00 |
| GRB7 | −1.93 | −3.01 | 2.98 | 0.00 |
| MYBL2 | −3.91 | −4.78 | 2.91 | 0.01 |
| CEGP1 | −3.00 | −1.85 | −2.89 | 0.01 |
| SURV | −4.23 | −5.06 | 2.88 | 0.01 |
| LMNB1 | −2.40 | −2.91 | 2.81 | 0.01 |
| CTSL2 | −5.74 | −6.39 | 2.83 | 0.01 |
| PTTG1 | −3.49 | −4.14 | 2.72 | 0.01 |
| BAG1 | −1.76 | −1.30 | −2.58 | 0.01 |
| KNSL2 | −3.35 | −4.06 | 2.60 | 0.01 |
| CIAP1 | −4.44 | −4.02 | −2.58 | 0.01 |
| PREP | −3.34 | −3.74 | 2.56 | 0.01 |
| NEK2 | −5.25 | −5.80 | 2.53 | 0.01 |
| EpCAM | −1.95 | −2.31 | 2.50 | 0.01 |
| PCNA | −2.79 | −3.13 | 2.42 | 0.02 |
| C20_orf1 | −2.48 | −3.09 | 2.39 | 0.02 |
| ITGA7 | −4.53 | −3.87 | −2.37 | 0.02 |

TABLE 1-continued

| Gene | Mean group A Event | Mean group B No event | T statistic | P value |
|---|---|---|---|---|
| ID1 | −2.58 | −2.17 | −2.30 | 0.02 |
| B_Catenin | −1.32 | −1.08 | −2.28 | 0.03 |
| EstR1 | −0.78 | −0.12 | −2.28 | 0.03 |
| CDH1 | −2.76 | −3.27 | 2.20 | 0.03 |
| TS | −2.86 | −3.29 | 2.18 | 0.03 |
| HER2 | 0.53 | −0.22 | 2.18 | 0.03 |
| cMYC | −3.22 | −2.85 | −2.16 | 0.04 |

In the foregoing Table 1, negative t-values indicate higher expression, associated with better outcomes, and, inversely, higher (positive) t-values indicate higher expression associated with worse outcomes. Thus, for example, elevated expression of the CCNB1 gene (t-value=3.02; CT mean alive<CT mean deceased) indicates a reduced likelihood of disease free survival. Similarly, elevated expression of the GSTM1 gene (t-value=−3.56; CT mean alive>CT mean deceased) indicates an increased likelihood of disease free survival.

Thus, based on the data set forth in Table 1, the expression of any of the following genes in breast cancer indicates a reduced likelihood of survival without cancer recurrence: C20_orf1; CCNB1; CDC20; CDH1; CTSL2; EpCAM; GRB7; HER2; KNSL2; LMNB1; MCM2; MMP9; MYBL2; NEK2; PCNA; PREP; PTTG1; STMY3; SURV; TS; MELK.

Based on the data set forth in Table 1, the expression of any of the following genes in breast cancer indicates a better prognosis for survival without cancer recurrence: BAG1; BCatenin; CEGP1; CIAP1; cMYC; DKFZp586M07; EstR1; GSTM1; GSTM3; ID1; ITGA7; PR.

Analysis of Multiple Genes and Indicators of Outcome

Two approaches were taken in order to determine whether using multiple genes would provide better discrimination between outcomes. First, a discrimination analysis was performed using a forward stepwise approach. Models were generated that classified outcome with greater discrimination than was obtained with any single gene alone. According to a second approach (time-to-event approach), for each gene a Cox Proportional Hazards model (see, e.g. Cox, D. R., and Oakes, D. (1984), *Analysis of Survival Data*, Chapman and Hall, London, N.Y.) was defined with time to recurrence or death as the dependent variable, and the expression level of the gene as the independent variable. The genes that have a p-value <0.05 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending on whether the gene is an indicator of bad (RR>1.01) or good (RR<1.01) prognosis. Thus, any threshold value will define subgroups of patients with respectively increased or decreased risk. The results are summarized in Table 2, which lists the 42 genes for which the p-value for the differences between the groups was <0.05.

TABLE 2

| Gene | Relative Risk | p-value |
|---|---|---|
| GRB7 | 1.52 | 0.000011 |
| SURV | 1.57 | 0.000090 |
| PR | 0.74 | 0.000129 |
| LMNB1 | 1.92 | 0.000227 |
| MYBL2 | 1.46 | 0.000264 |
| HER2 | 1.46 | 0.000505 |
| GSTM1 | 0.68 | 0.000543 |
| MELK | 1.59 | 0.000684 |
| C20_orf1 | 1.59 | 0.000735 |
| PTTG1 | 1.63 | 0.001135 |
| BUB1 | 1.58 | 0.001425 |
| CDC20 | 1.54 | 0.001443 |
| CCNB1 | 1.60 | 0.001975 |
| STMY3 | 1.47 | 0.002337 |
| KNSL2 | 1.48 | 0.002910 |
| CTSL2 | 1.43 | 0.003877 |
| MCM2 | 1.59 | 0.005203 |
| NEK2 | 1.48 | 0.006533 |
| DR5 | 0.62 | 0.006660 |
| Ki_67 | 1.46 | 0.008188 |
| CCNE2 | 1.38 | 0.009505 |
| TOP2A | 1.38 | 0.009551 |
| PCNA | 1.67 | 0.010237 |
| PREP | 1.69 | 0.012308 |
| FOXM1 | 1.52 | 0.012837 |
| NME1 | 1.46 | 0.013622 |
| CEGP1 | 0.84 | 0.013754 |
| BAG1 | 0.68 | 0.015422 |
| STK15 | 1.46 | 0.017013 |
| HNRPAB | 1.96 | 0.017942 |
| EstR1 | 0.80 | 0.018877 |
| MMP9 | 1.19 | 0.019591 |
| DKFZp586M07 | 0.79 | 0.020073 |
| TS | 1.44 | 0.025186 |
| Src | 1.70 | 0.037398 |
| BIN1 | 0.75 | 0.038979 |
| NPD009 | 0.80 | 0.039020 |
| RPLPO | 0.52 | 0.041575 |
| GSTM3 | 0.84 | 0.041848 |
| MMP12 | 1.27 | 0.042074 |
| TFRC | 1.57 | 0.046145 |
| IGF1R | 0.78 | 0.046745 |

Based on the data set forth in Table 2, the expression of any of the following genes in breast cancer indicates a reduced likelihood of survival without cancer recurrence: GRB7; SURV; LMNB1; MYBL2; HER2; MELK; C20_orf1; PTTG1; BUB1; CDC20; CCNB1; STMY3; KNSL2; CTSL2; MCM2; NEK2; Ki_67; CCNE2; TOP2A-4; PCNA; PREP; FOXM1; NME1; STK15; HNRPAB; MMP9; TS; Src; MMP12; TFRC.

Based on the data set forth in Table 2, the expression of any of the following genes in breast cancer indicates a better prognosis for survival without cancer recurrence: PR; GSTM1; DR5; CEGP1; BAG1; EstR1; DKFZp586M07; BIN1; NPD009; RPLPO; GSTM3; IGF1R.

The binary and time-to-event analyses, with few exceptions, identified the same genes as prognostic markers. For example, comparison of Tables 1 and 2 shows that 10 genes were represented in the top 15 genes in both lists. Furthermore, when both analyses identified the same gene at [p<0.10], which happened for 26 genes, they were always concordant with respect to the direction (positive or negative sign) of the correlation with survival/recurrence. Overall, these results strengthen the conclusion that the identified markers have significant prognostic value.

Multivariate Gene Analysis of 242 Patients with Invasive Breast Carcinoma

For Cox models comprising more than two genes (multivariate models), stepwise entry of each individual gene into the model is performed, where the first gene entered is pre-selected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis was performed using the following equation:

$$RR = \exp[\text{coef}(\text{geneA}) \times Ct(\text{geneA}) + \text{coef}(\text{geneB}) \times Ct(\text{geneB}) + \text{coef}(\text{geneC}) \times Ct(\text{geneC}) + \ldots].$$

In this equation, coefficients for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

A multivariate stepwise analysis, using the Cox Proportional Hazards Model, was performed on the gene expression data obtained for all 242 patients with invasive breast carcinoma. The following ten-gene set has been identified by this analysis as having particularly strong predictive value of patient survival: GRB7; LMNB1; ER; STMY3; KLK10; PR; KRT5; FGFR1; MCM6; SNRPF. In this gene set ER, PR, KRT5 and MCM6 contribute to good prognosis, while GRB7, LMNB1, STMY3, KLK10, FGFR1, and SNRPF contribute to poor prognosis.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the personalized prognosis of breast cancer, similar genes, gene sets and methods concerning other types of cancer are specifically within the scope herein. In particular, the present gene sets or variants thereof can be used as prognostic markers to predict the likelihood of long-term survival or cancer recurrence in the case of ovarian cancer.

All references cited throughout the disclosure are hereby expressly incorporated by reference.

TABLE 3

| Gene | Accession | Start | Stop | SEQ ID NO. | Sequence |
|---|---|---|---|---|---|
| B-Catenin | NM_001904 | 1549 | 1629 | SEQ ID NO: 1 | GGCTCTTGTGCGTACTGTCCTTCGGGCTGGTGACAGGGAAGACATCACTGAGCCTGCCATCTGTGCTCTTCGTCATCTGA |
| BAG1 | NM_004323 | 673 | 754 | SEQ ID NO: 2 | CGTTGTCAGCACTTGGAATACAAGATGGTTGCCGGGTCATGTTAATTGGGAAAAGAACAGTCCACAGGAAGAGGTTGAAC |
| BIN1 | NM_004305 | 866 | 942 | SEQ ID NO: 3 | CCTGCAAAAGGGAACAAGAGCCCTTCGCCTCCAGATGCTCCCCTGCCGCCACCCCGAGATCAGAGTCAACCACG |
| BUB1 | NM_004336 | 1002 | 1070 | SEQ ID NO: 4 | CCGAGGTTAATCCAGCACACGTAGGCTCCCAGGAACTGAGAGCCCATGTCTT |
| C20 orf1 | NM_012112 | 2675 | 2740 | SEQ ID NO: 5 | TCAGCTGTGAGCTGCGATACCGCCCGGCAATGGGACTTGCTCTCTTAACCTCAAACCTAGGACCGT |
| CCNB1 | NM_031966 | 823 | 907 | SEQ ID NO: 6 | TTTCAGGTTGTTGCAGGAGACCATGTACATGACTGTCTCCATTATTGATCGGTTCATGCAGAATAATGTGCCCAAGAAGATG |
| CCNE2 | NM_057749 | 2026 | 2108 | SEQ ID NO: 7 | ATGCTGTGGCTCCTTCCTAACTGGGCTTTCTTGACATGTAGGTTGCTTGGTAATAACCTTTTTGTATATCACAATTTGGGT |
| CDC20 | NM_001255 | 679 | 747 | SEQ ID NO: 8 | TGGATTGGAGTTCTGGAATGTACTGCCCCGCGACACTGGCCGTGGACAACAGTGTTGTACCTGTGAGTGCAAGC |
| CDH1 | NM_004360 | 2499 | 2580 | SEQ ID NO: 9 | TGAGTGTCCCCCGGTATCTTCCCCCGCCAATCTGCCAATCTCCGATGAAATTTTATTGATGAAAATCTGAAAGCGGCTG |
| CEGP1 | NM_020974 | 563 | 640 | SEQ ID NO: 10 | TGACAATCAGCACCATGCATTCACCGCTCAGTGGAACCAAAGATGATCTATGTCAGAACACCGAGGCATTTTCC |
| CIAP1 | NM_001166 | 1822 | 1894 | SEQ ID NO: 11 | TGCCTGTGGTGGGAAGCTCAGTAACTGGAACCAAAGATCTCCAAGGGGTCAAGTTGGACAGTGTCAGATCCTGAGACAGATCAGCAACAACCG |
| cMYC | NM_002467 | 1494 | 1578 | SEQ ID NO: 12 | TCCCTCCACTCGGAAGGACTATCCTGCTGCCAAGAATCTGTGGACTTGTTCGCGTCCTCCAAGGACTGTGCAGCCAATCAGGGCTGCAATGGT |
| CTSL2 | NM_001333 | 671 | 738 | SEQ ID NO: 13 | TGTCTCACTGAGCGAGCAGAATCTGTGGACTTGTTCGCGTCCTCCAAGGACTGTGCAGCCAATCAGGGCTGCAATGGT |
| DKFzp586 | AL050227 | 559 | 633 | SEQ ID NO: 14 | TCCATTTTCTACCTGTTAACCTTCATCATTTTGCAGACTTTGTTGACACTTGGTCCTGACTTGTGCAGGCCCTGCCCCTTTGACTCCTGGAAGCCCTCATGAGGAAGTTGGCCTCATGG |
| DR5 | NM_003842 | 1127 | 1211 | SEQ ID NO: 15 | CTCTGAGACAGTGCTTCGATGACTTTGCAGACTTGTCCTGACTGCGATGAGAGCGGGCTCTTTAAGGCCAAGCAGTGCA |
| EpCAM | NM_002354 | 435 | 510 | SEQ ID NO: 16 | GGGGACCCTCCAGAACAATGATGGGCTTTATGATCCTGACTGCGATGCGACGCCCACCGCCTACATGCGCCCACTAGCC |
| EstR1 | NM_000125 | 1956 | 2024 | SEQ ID NO: 17 | CGTGTGCCCCTCTATGACCTGCTGCTGGAGATGCTGGACGCCCACCGCCTGTGAAGTGGATGGCACCC |
| FGFR1 | NM_023109 | 2685 | 2759 | SEQ ID NO: 18 | CACGGACATTCACCACATCGACTACTATAAAAAGACAACCAACGGCCAGCTGCCACTGCCTGTGAAGTGGATGGCACCC |
| FOXM1 | NM_021953 | 1898 | 1980 | SEQ ID NO: 19 | CCACCCCGAGCAATCTGTCTCCCCAGAACCCCTGAATCCTGAGGCTCACGCGCCCCAGCCAAAGTAGGGGGACTGATTT |
| GRB7 | NM_005310 | 1275 | 1342 | SEQ ID NO: 20 | CCATCTGCATCCATCCATCTGTTTTGGGCTCCCACCCTTGAGAAGTGCCTCAGATAATACCCTGGTGCC |

TABLE 3-continued

| Gene | Accession | Start | Stop | SEQ ID NO. | Sequence |
|---|---|---|---|---|---|
| GSTM1 | NM_000561 | 93 | 179 | SEQ ID NO: 21 | AAGTATGAGGAAAAGAAGTACACGATGGGGACGCTCCTGATTATGACAGAGCCAGTGGCTGAATGAAAAATTCAAGCTGGGCC |
| GSTM3 | NM_000849 | 248 | 324 | SEQ ID NO: 22 | CAATGCCATCTTGCCGTACATCGCTCGCAAGCACACAACATGTGTGAGAAGAAAAGATTCGAGTGAC |
| HER2 | NM_004448 | 1138 | 1208 | SEQ ID NO: 23 | CGGTGTGAGAAGTGCAGCAAGCCCTGTGCCCGAGTGTGCTATGGTCTGGGCATGGAGCACTTGCGAGAGG |
| HNRPAB | NM_004499 | 1086 | 1170 | SEQ ID NO: 24 | CAAGGAGCGACCAACTGATCGCACACATGTCTTTGTTTGGATATGAGTGAACACAATTATGTACCAAATTTAACTTGCAAAC |
| ID1 | NM_002165 | 286 | 356 | SEQ ID NO: 25 | AGAACCGCAAGGTGAGCAAGGTGGAGATTCTCCAGCACGTCATCGACTACATCAGGGACCTTCAGTTGA |
| IGF1R | NM_000875 | 3467 | 3550 | SEQ ID NO: 26 | GCATGGTAGCCGAGATTTCACAGTCTCAAAATCGAGATTTTGTATGACGCGAGATATCTATGAGACAGACTATTACCGAAA |
| ITGA7 | NM_002206 | 633 | 712 | SEQ ID NO: 27 | GATATGATTGGTCGCTGCTTTGTGCTCAGCCAGGACCTGGCCATCCCGGATGAGTTGGATGGTGGGAATGGGAAGTTCT |
| KI-67 | NM_002417 | 42 | 122 | SEQ ID NO: 28 | CGGACTTTGGGTTGCCGACTTGTCCGAGGCGGTGGTTCGACAGAAGTGGCCTTGCGGGGCCGATCGTCCCAGTGAAGAGTTGTAA |
| KLK10 | NM_002776 | 966 | 1044 | SEQ ID NO: 29 | GCCCAGAGAGGCTCCATCGCCATCCTTCCTCCCCAGTCGGCTCGAACTCTCCCCTTGTCTGCACTGTTCAAACCTCTG |
| KNSL2 | BC000712 | 1266 | 1343 | SEQ ID NO: 30 | CCAACTCGCCATGATGATTTTTCCTTTGACCGGTATTCCCACCAGGAAGTGGACAGGATGAAGTGTTTGAAGAGATTGC |
| KRT5 | NM_000424 | 1605 | 1674 | SEQ ID NO: 31 | TCAGTGGAGAAGGAGTTGGACAGTTGTCACAGCAGTGTTTCCTCTGGATATGGCA |
| LMNB1 | NM_005573 | 1500 | 1566 | SEQ ID NO: 32 | TGCAAACGCTGGTGTCACAGCCTACCTTTCATTCCGGCCTGACAACAATGAGCTGTTGCTCTTTCATACTGAAGCAGTTAGTGG |
| MCM2 | NM_004526 | 2442 | 2517 | SEQ ID NO: 33 | GACTTTTGCCCGCTACTTTCATTCACACATTCATCACAGTTTCATACCAACAGCCGTCCTCTTTGGTGTCTTTCCTGTCCA |
| MCM6 | NM_005915 | 2669 | 2751 | SEQ ID NO: 34 | TGATGGTCCTATGTCTCACATTCTCACAATTCATCACAGGCTTCAGCAGCTTCAGAGGACACTTCCTTTGGTGTCTTTCCTGTCCA |
| MELK | NM_014791 | 22 | 87 | SEQ ID NO: 35 | AACCCGGACGATCGAAAAGATTCTTAGGAACGCCGTACCAGCCGCTCTCTCAGGACAGCAGGCCC |
| MMP12 | NM_002426 | 816 | 894 | SEQ ID NO: 36 | CCAACGCTTGCCCAAATCTTCCACCAGCAGCAACTTCAGAACCTGTGCCCCAATTTGAGTTGATGCTGTCACTACCGT |
| MMP9 | NM_004994 | 124 | 191 | SEQ ID NO: 37 | GAGAACCAATCTCACCGACGCAGCTGCAGAGGAATACCTGTACCGCTATGGTTACACTCGGGTG |
| MYBL2 | NM_002466 | 599 | 673 | SEQ ID NO: 38 | GCCGAGATCGCCAAGATGTTGCCAGGAGGACAGACAATGCTGTGAAGAATCACTGGAACTCTACCATCAAAAG |
| NEK2 | NM_002497 | 102 | 181 | SEQ ID NO: 39 | GTGAGGCAGCGCGACTCTGCGCATGCCCGCGACTGGGCCATGGCCTCAGGACTATGAAGTGTTGTACACCATTGGCA |
| NME1 | NM_000269 | 365 | 439 | SEQ ID NO: 40 | CCAACCCTGCAGACTTCCAAGCCTCCATCCGTGGACCATCCCAGATCTCTGCATACAAGTTGCAGGAACATTATACAT |

TABLE 3-continued

| Gene | Accession | Start | Stop | SEQ ID NO. | Sequence |
|---|---|---|---|---|---|
| NPD009 | NM_020686 | 589 | 662 | SEQ ID NO: 41 | GGCTGTGGCTGTGAGGCTGTAGCATCTCTGCTGGAGGTGAGACACTCTGGGAACTGATTTGACCTCGAATGCTCC |
| PCNA | NM_002592 | 157 | 228 | SEQ ID NO: 42 | GAAGGTGTTGGAGGCACTCAAGGACCTCATCAACGAGGCCTGCTGGGATATTAGCTCCAGCGGTGTAAACC |
| PR | NM_000926 | 1895 | 1980 | SEQ ID NO: 43 | GCATCAGGCTGTCATTATGGTGTCCTTACCTGTGGGAGCTGTAAGGTCTTCTTTAAGAGGGCAATGGAAGGGCAGCACAACTACT |
| PREP | NM_002726 | 889 | 965 | SEQ ID NO: 44 | GGGACGGTGTTCACATTCAAGACGAATCGCCAGTCTCCCAACTATCGCGTGATCAACATTGACTTCTGGGATCCTG |
| PTTG1 | NM_004219 | 48 | 122 | SEQ ID NO: 45 | GGCTACTCTGATCTATGTTGATAAGGAAAATGAGAACGACCCGTGTGTTGCTAAGGATGGGCTGAAGC |
| RPLP0 | NM_001002 | 791 | 866 | SEQ ID NO: 46 | CCAATTCTATCATCAACGGGTACAAACGAGTCCTGCCCTTGTCTGTGGAGACGGATTACACCTTCCCACTTGCTGA |
| SNRPF | NM_003095 | 71 | 150 | SEQ ID NO: 47 | GGCTGGTCGGCAGAGAGTAGCCTGCAAACATTCGCCGTTGTTTACATGAGTTTACCCCTCAATCCAAACCTTTCCTCA |
| Src | NM_004383 | 979 | 1043 | SEQ ID NO: 48 | CCTGAACATGAAAGAGCTGCTGCAGAACATCGTGAAGCTCTCTGTGGCACCCTGGACTACCTGCCCCTGAAATGATTGAAGGTCGGA |
| STK15 | NM_003600 | 1101 | 1170 | SEQ ID NO: 49 | CATCTTCCAGGAGGAGGACCACTCTCTGTGGCACCCTGGACTACCTGCCCCTGAAATGATTGAAGGTCGGA |
| STMY3 | NM_005940 | 2090 | 2180 | SEQ ID NO: 50 | CCTGGAGGCTGCAACATACCTCTCTGTCCCAGGCCGATCCTCTGAAGCCCTTTTCGCAGCACTGCTATCCTCCAAAGCCATTGTA |
| SURV | NM_001168 | 737 | 817 | SEQ ID NO: 51 | TGTTGATTCCCGGGCTTACCAGTGAGAAGTGAGGAGGAAGGCAGTGTCCCTTTTGCTAGAGCTGACAGCTTG |
| TFRC | NM_003234 | 2110 | 2178 | SEQ ID NO: 52 | GCCAACTGCTTTCATTTGTGAGGGATCTGAACCAATAACAGAGCAGACATAAAGGAAATGGGCCTGAGT |
| TOP2A | NM_001067 | 4505 | 4577 | SEQ ID NO: 53 | AATCCAAGGGGAGAGTGATGACTTCCATATGGACTTTGACTGTGCCTCCTCGGGCAAAATCTGTAC |
| TS | NM_001071 | 764 | 829 | SEQ ID NO: 54 | GCCTCGGTGTGCCTTTCAACATCCAGCTACGCCCTGCTCACGTACGTACTACAATGCCACATCACG |

TABLE 4A

| Gene | Accession | Name | SEQ ID NO | Sequence | |
|---|---|---|---|---|---|
| B-Catenin | NM_001904 | S2150/B-Cate.f3 | SEQ ID NO:55 | GGCTCTTGTGCGTACTGTCCTT | 22 |
| B-Catenin | NM_001904 | S2151/B-Cate.r3 | SEQ ID NO:56 | TCAGATGACGAAGAGCACAGATG | 23 |
| B-Catenin | NM_001904 | S50461B-Cate.p3 | SEQ ID NO:57 | AGGCTCAGTGATGTCTTCCCTGTCACCAG | 29 |
| BAG1 | NM_004323 | S1386/BAG1.f2 | SEQ ID NO:58 | CGTTGTCAGCACTTGGAATACAA | 23 |
| BAG1 | NM_004323 | S1387/BAG1.r2 | SEQ ID NO:59 | GTTCAACCTCTTCCTGTGGACTGT | 24 |
| BAG1 | NM_004323 | S4731/BAG1.p2 | SEQ ID NO:60 | CCCAATTAACATGACCCGGCAACCAT | 26 |
| BIN1 | NM_004305 | S2651/BIN1.f3 | SEQ ID NO:61 | CCTGCAAAAGGGAACAAGAG | 20 |
| BIN1 | NM_004305 | S2652/BIN1.r3 | SEQ ID NO:62 | CGTGGTTGACTCTGATCTCG | 20 |
| BIN1 | NM_004305 | S4954/BIN1.p3 | SEQ ID NO:63 | CTTCGCCTCCAGATGGCTCCC | 21 |
| BUB1 | NM_004336 | S4294/BUB1.f1 | SEQ ID NO:64 | CCGAGGTTAATCCAGCACGTA | 21 |
| BUB1 | NM_004336 | S4295/BUB1.r1 | SEQ ID NO:65 | AAGACATGGCGCTCTCAGTTC | 21 |
| BUB1 | NM_004336 | S4296/BUB1.p1 | SEQ ID NO:66 | TGCTGGGAGCCTACACTTGGCCC | 23 |
| C20 orf1 | NM_012112 | S3560/C20 or.f1 | SEQ ID NO:67 | TCAGCTGTGAGCTGCGGATA | 20 |
| C20 orf1 | NM_012112 | S3561/C20 or.r1 | SEQ ID NO:68 | ACGGTCCTAGGTTTGAGGTTAAGA | 24 |
| C20 orf1 | NM_012112 | S3562/C20 or.p1 | SEQ ID NO:69 | CAGGTCCCATTGCCGGGCG | 19 |
| CCNB1 | NM_031966 | S1720/CCNB1.f2 | SEQ ID NO:70 | TTCAGGTTGTTGCAGGAGAC | 20 |
| CCNB1 | NM_031966 | S1721/CCNB1.r2 | SEQ ID NO:71 | CATCTTCTTGGGCACACAAT | 20 |
| CCNB1 | NM_031966 | S4733/CCNB1.p2 | SEQ ID NO:72 | TGTCTCCATTATTGATCGGTTCATGCA | 27 |
| CCNE2 | NM_057749 | S1458/CCNE2.f2 | SEQ ID NO:73 | ATGCTGTGGCTCCTTCCTAACT | 22 |
| CCNE2 | NM_057749 | S1459/CCNE2.r2 | SEQ ID NO:74 | ACCCAAATTGTGATATACAAAAAGGTT | 27 |
| CCNE2 | NM_057749 | S4945/CCNE2.p2 | SEQ ID NO:75 | TACCAAGCAACCTACATGTCAAGAAAGCCC | 30 |
| CDC20 | NM_001255 | S4447/CDC20.f1 | SEQ ID NO:76 | TGGATTGGAGTTCTGGGAATG | 21 |
| CDC20 | NM_001255 | S4448/CDC20.r1 | SEQ ID NO:77 | GCTTGCACTCCACAGGTACACA | 22 |
| CDC20 | NM_001255 | S4449/CDC20.p1 | SEQ ID NO:78 | ACTGGCCGTGGCACTGGACAACA | 23 |
| CDH1 | NM_004360 | S0073/CDH1.f3 | SEQ ID NO:79 | TGAGTGTCCCCCGGTATCTTC | 21 |
| CDH1 | NM_004360 | S0075/CDH1.r3 | SEQ ID NO:80 | CAGCCGCTTTCAGATTTTCAT | 21 |
| CDH1 | NM_004360 | S4990/CDH1.p3 | SEQ ID NO:81 | TGCCAATCCCGATGAAATTGGAAATTT | 27 |
| CEGP1 | NM_020974 | S1494/CEGP1.f2 | SEQ ID NO:82 | TGACAATCAGCACACCTGCAT | 21 |
| CEGP1 | NM_020974 | S1495/CEGP1.r2 | SEQ ID NO:83 | TGTGACTACAGCCGTGATCCTTA | 23 |
| CEGP1 | NM_020974 | S4735/CEGP1.p2 | SEQ ID NO:84 | CAGGCCCTCTTCCGAGCGGT | 20 |
| CIAP1 | NM_001166 | S0764/CIAP1.f2 | SEQ ID NO:85 | TGCCTGTGGTGGGAAGCT | 18 |
| CIAP1 | NM_001166 | S0765/CIAP1.r2 | SEQ ID NO:86 | GGAAAATGCCTCCGGTGTT | 19 |
| CIAP1 | NM_001166 | S4802/C1AP1.p2 | SEQ ID NO:87 | TGACATAGCATCATCCTTTGGTTCCCAGTT | 30 |
| cMYC | NM_002467 | S0085/cMYC.f3 | SEQ ID NO:86 | TCCCTCCACTCGGAAGGACTA | 21 |
| cMYC | NM_002467 | S0087/cMYC.r3 | SEQ ID NO:89 | CGGTTGTTGCTGATCTGTCTCA | 22 |
| cMYC | NM_002467 | S4994/cMYC.p3 | SEQ ID NO:90 | TCTGACACTGTCCAACTTGACCCTCTT | 27 |
| CTSL2 | NM_001333 | S4354/CTSL2.f1 | SEQ ID NO:91 | TGTCTCACTGAGCGAGCAGAA | 21 |
| CTSL2 | NM_001333 | S4355/CTSL2.r1 | SEQ ID NO:92 | ACCATTGCAGCCCTGATTG | 19 |
| CTSL2 | NM_001333 | S4356/CTSL2.p1 | SEQ ID NO:93 | CTTGAGGACGCGAACAGTCCACCA | 24 |

TABLE 4A-continued

| Gene | Accession | Name | SEQ ID NO | Sequence | |
|---|---|---|---|---|---|
| DKFZp586M0723 | AL050227 | S4396/DKFZp5.f1 | SEQ ID NO:94 | TCCATTTTCTACCTGTTAACCTTCATC | 27 |
| DKFZp586M0723 | AL050227 | S4397/DKFZp5.r1 | SEQ ID NO:95 | ATGCAGTCGGTCCCTTCCT | 19 |
| DKFZp586M0723 | AL050227 | S4398/DKFZpS.p1 | SEQ ID NO:96 | TTGCTTCCAGGGCCTGCACAAAA | 23 |
| DR5 | NM_003842 | S2551/DR5.f2 | SEQ ID NO:97 | CTCTGAGACAGTGCTTCGATGACT | 24 |
| DR5 | NM_003842 | S2552/DR5.r2 | SEQ ID NO:98 | CCATGAGGCCCAACTTCCT | 19 |
| DR5 | NM_003842 | S4979/DR5.p2 | SEQ ID NO:99 | CAGACTTGGTGCCCTTTGACTCC | 23 |
| EpCAM | NM_002354 | S1807/EpCAM.f1 | SEQ ID NO:100 | GGGCCCTCCAGAACAATGAT | 20 |

TABLE 4B

| Gene | Accession | Name | SEQ ID NO | Sequence | |
|---|---|---|---|---|---|
| EpCAM | NM_002354 | S1808/EpCAM.r1 | SEQ ID NO:101 | TGCACTGCTTGGCCTTAAAGA | 21 |
| EpCAM | NM_002354 | S4984/EpCAM.p1 | SEQ ID NO:102 | CCGCTCTCATCGCAGTCAGGATCAT | 25 |
| EstR1 | NM_000125 | S0115/EstR1.f1 | SEQ ID NO:103 | CGTGGTGCCCCTCTATGAC | 19 |
| EstR1 | NM_000125 | S0117/EstR1.r1 | SEQ ID NO:104 | GGCTAGTGGGCGCATGTAG | 19 |
| EstR1 | NM_000125 | S4737/EstR1.p1 | SEQ ID NO:105 | CTGGAGATGCTGGACGCCC | 19 |
| FGFR1 | NM_023109 | S0818/FGFR1.f3 | SEQ ID NO:106 | CACGGGACATTCACCACATC | 20 |
| FGFR1 | NM_023109 | S0819/FGFR1.r3 | SEQ ID NO:107 | GGGTGCCATCCACTTCACA | 19 |
| FGFR1 | NM_023109 | S4816/FGFR1.p3 | SEQ ID NO:108 | ATAAAAAGACAACCAACGGCCGACTGC | 27 |
| FOXM1 | NM_021953 | S2006/FOXM1.f1 | SEQ ID NO:109 | CCACCCCGAGCAAATCTGT | 19 |
| FOXM1 | NM_021953 | S2007/FOXM1.r1 | SEQ ID NO:110 | AAATCCAGTCCCCCTACTTTGG | 22 |
| FOXM1 | NM_021953 | S4757/FOXM1.p1 | SEQ ID NO:111 | CCTGAATCCTGGAGGCTCACGCC | 23 |
| GRB7 | NM_005310 | S0130/GRB7.f2 | SEQ ID NO:112 | ccatctgcatccatcftgft | 20 |
| GRB7 | NM_005310 | S0132/GRB7.r2 | SEQ ID NO:113 | ggccaccagggtattatctg | 20 |
| GRB7 | NM_005310 | S4726/GRB7.p2 | SEQ ID NO:114 | ctccccacccttgagaagtgcct | 23 |
| GSTM1 | NM_000561 | S2026/GSTM1.r1 | SEQ ID NO:115 | GGCCCAGCTTGAATTTTTCA | 20 |
| GSTM1 | NM_000561 | S2027/GSTM1.f1 | SEQ ID NO:116 | AAGCTATGAGGAAAAGAAGTACACGAT | 27 |
| GSTM1 | NM_000561 | S4739/GSTM1.p1 | SEQ ID NO:117 | TCAGCCACTGGCTTCTGTCATAATCAGGAG | 30 |
| GSTM3 | NM_000849 | S2038/GSTM3.f2 | SEQ ID NO:118 | CAATGCCATCTTGCGCTACAT | 21 |
| GSTM3 | NM_000849 | S2039/GSTM3.r2 | SEQ ID NO:119 | GTCCACTCGAATCTTTTCTTCA | 25 |
| GSTM3 | NM_000849 | S5064/GSTM3.p2 | SEQ ID NO:120 | CTCGCAAGCACAACATGTGTGGTGAGA | 27 |
| HER2 | NM_004448 | S0142/HER2.f3 | SEQ ID NO:121 | CGGTGTGAGAAGTGCAGCAA | 20 |
| HER2 | NM_004448 | S0144/HER2.r3 | SEQ ID NO:122 | CCTCTCGCAAGTGCTCCAT | 19 |
| HER2 | NM_004448 | S4729/HER2.p3 | SEQ ID NO:123 | CCAGACCATAGCACACTCGGGCAC | 24 |
| HNRPAB | NM_004499 | S4510/HNRPAB.f3 | SEQ ID NO:124 | CAAGGGAGCGACCAACTGA | 19 |
| HNRPAB | NM_004499 | S4511/HNRPAB.r3 | SEQ ID NO:125 | GTTTGCCAAGTTAAATTTGGTACATAAT | 28 |
| HNRPAB | NM_004499 | S4512/HNRPAB.p3 | SEQ ID NO:126 | CTCCATATCCAAACAAAGCATGTGTGCG | 28 |
| ID1 | NM_002165 | S0820/ID1.f1 | SEQ ID NO:127 | AGAACCGCAAGGTGAGCAA | 19 |
| ID1 | NM_002165 | S0821/ID1.r1 | SEQ ID NO:128 | TCCAACTGAAGGTCCCTGATG | 21 |
| ID1 | NM_002165 | S4832/ID1.p1 | SEQ ID NO:129 | TGGAGATTCTCCAGCACGTCATCGAC | 26 |

TABLE 4B-continued

| | | | | |
|---|---|---|---|---|
| IGF1R | NM_000875 | S1249/IGF1R.f3 | SEQ ID NO:130 GCATGGTAGCCGAAGATTTCA | 21 |
| IGF1R | NM_000875 | S1250/IGF1R.r3 | SEQ ID NO:131 TTTCCGGTAATAGTCTGTCTCATAGATATC | 30 |
| IGF1R | NM_000875 | S4895/IGF1R.p3 | SEQ ID NO:132 CGCGTCATACCAAAATCTCCGATTTTGA | 28 |
| ITGA7 | NM_002206 | S0859/ITGA7.f1 | SEQ ID NO:133 GATATGATTGGTCGCTGCTTTG | 22 |
| ITGA7 | NM_002206 | S0920/ITGA7.r1 | SEQ ID NO:134 AGAACTTCCATTCCCCACCAT | 21 |
| ITGA7 | NM_002206 | S4795/ITGA7.p1 | SEQ ID NO:135 CAGCCAGGACCTGGCCATCCG | 21 |
| KI-67 | NM_002417 | S0436/Ki-67.f2 | SEQ ID NO:136 CGGACTTTGGGTGCGACTT | 19 |
| Ki-67 | NM_002417 | S0437/Ki-67.r2 | SEQ ID NO:137 TTACAACTCTTCCACTGGGACGAT | 24 |
| Ki-67 | NM_002417 | S4741/Ki-67.p2 | SEQ ID NO:138 CCACTTGTCGAACCACCGCTCGT | 23 |
| KLK10 | NM_002776 | S2624/KLK10.f3 | SEQ ID NO:139 GCCCAGAGGCTCCATCGT | 18 |
| KLK10 | NM_002776 | S2625/KLK10.r3 | SEQ ID NO:140 CAGAGGTTTGAACAGTGCAGACA | 23 |
| KLK10 | NM_002776 | S4978/KLK10.p3 | SEQ ID NO:141 CCTCTTCCTCCCCAGTCGGCTGA | 23 |
| KNSL2 | BC000712 | S4432/KNSL2.f2 | SEQ ID NO:142 CCACCTCGCCATGATTTTTC | 20 |
| KNSL2 | BC000712 | S4433/KNSL2.r2 | SEQ ID NO:143 GCAATCTCTTCAAACACTTCATCCT | 25 |
| KNSL2 | BC000712 | S4434/KNSL2.p2 | SEQ ID NO:144 TTTGACCGGGTATTCCCACCAGGAA | 25 |
| KRT5 | NM_000424 | S0175/KRT5.f3 | SEQ ID NO:145 tcagtggagaaggagttgga | 20 |
| KRT5 | NM_000424 | S0177/KRT5.r3 | SEQ ID NO:146 tgccatatccagaggaaaca | 20 |
| KRT5 | NM_000424 | S5015/KRT5.p3 | SEQ ID NO:147 ccagtcaacatctctgttgtcacaagca | 28 |
| LMNB1 | NM_005573 | S4477/LMNB1.f1 | SEQ ID NO:148 TGCAAACGCTGGTGTCACA | 19 |

TABLE 4C

| | | | | |
|---|---|---|---|---|
| LMNB1 | NM_005573 | S4478/LMNB1.r1 | SEQ ID NO:149 CCCCACGAGTTCTGGTTCTTC | 21 |
| LMNB1 | NM_005573 | S4479/LMNB1.p1 | SEQ ID NO:150 CAGCCCCCCAACTGACCTCATC | 22 |
| MCM2 | NM_004526 | S1602/MCM2.f2 | SEQ ID NO:151 GACTTTTGCCCGCTACCTTTC | 21 |
| MCM2 | NM_004526 | S1603/MCM2.r2 | SEQ ID NO:152 GCCACTAACTGCTTCAGTATGAAGAG | 26 |
| MCM2 | NM_004526 | S4900/MCM2.p2 | SEQ ID NO:153 ACAGCTCATTGTTGTCACGCCGGA | 24 |
| MCM6 | NM_005915 | S1704/MCM6.f3 | SEQ ID NO:154 TGATGGTCCTATGTGTCACATTCA | 24 |
| MCM6 | NM_005915 | S1705/MCM6.r3 | SEQ ID NO:155 TGGGACAGGAAACACACCAA | 20 |
| MCM6 | NM_005915 | S4919/MCM6.p3 | SEQ ID NO:156 CAGGTTTCATACCAACACAGGCTTCAGCAC | 30 |
| MELK | NM_014791 | S4318/MELK.f1 | SEQ ID NO:157 AACCCGGCGATCGAAAAG | 18 |
| MELK | NM_014791 | S4319/MELK.r1 | SEQ ID NO:158 GGGCCTGCTGTCCTGAGA | 18 |
| MELK | NM_014791 | S4320/MELK.p1 | SEQ ID NO:159 TCTTAGGAACGCCGTACCAGCCGC | 24 |
| MMP12 | NM_002426 | S4381/MMP12.f2 | SEQ ID NO:160 CCAACGCTTGCCAAATCCT | 19 |
| MMP12 | NM_002426 | S4382/MMP12.r2 | SEQ ID NO:161 ACGGTAGTGACAGCATCAAAACTC | 24 |
| MMP12 | NM_002426 | S4383/MMP12.p2 | SEQ ID NO:162 AACCAGCTCTCTGTGACCCCAATT | 24 |
| MMP9 | NM_004994 | S0656/MMP9.f1 | SEQ ID NO:163 GAGAACCAATCTCACCGACA | 20 |
| MMP9 | NM_004994 | S0657/MMP9.r1 | SEQ ID NO:164 CACCCGAGTGTAACCATAGC | 20 |
| MMP9 | NM_004994 | S4760/MMP9.p1 | SEQ ID NO:165 ACAGGTATTCCTCTGCCAGCTGCC | 24 |
| MYBL2 | NM_002466 | S3270/MYBL2.f1 | SEQ ID NO:166 GCCGAGATCGCCAAGATG | 18 |

TABLE 4C-continued

| | | | | | |
|---|---|---|---|---|---|
| MYBL2 | NM_002466 | S3271/MYBL2.r1 | SEQ ID NO:167 | CTTTTGATGGTAGAGTTCCAGTGATTC | 27 |
| MYBL2 | NM_002466 | S4742/MYBL2.p1 | SEQ ID NO:168 | CAGCATTGTCTGTCCTCCCTGGCA | 24 |
| NEK2 | NM_002497 | S4327/NEK2.f1 | SEQ ID NO:169 | GTGAGGCAGCGCGACTCT | 18 |
| NEK2 | NM_002497 | S4328/NEK2.r1 | SEQ ID NO:170 | TGGCAATGGTGTACAACACTTCA | 23 |
| NEK2 | NM_002497 | S4329/NEK2.p1 | SEQ ID NO:171 | TGCCTTCCCGGGCTGAGGACT | 21 |
| NME1 | NM_000269 | S2526/NME1.f3 | SEQ ID NO:172 | CCAACCCTGCAGACTCCAA | 19 |
| NME1 | NM_000269 | S2527/NME1.r3 | SEQ ID NO:173 | ATGTATAATGTTCCTGCCAACTTGTATG | 28 |
| NME1 | NM_000269 | S4949/NME1.p3 | SEQ ID NO:174 | CCTGGGACCATCCGTGGAGACTTCT | 25 |
| NPD009 | NM_020686 | S4474/NPD009.f3 | SEQ ID NO:175 | GGCTGTGGCTGAGGCTGTAG | 20 |
| NPD009 | NM_020686 | S4475/NPD009.r3 | SEQ ID NO:176 | GGAGCATTCGAGGTCAAATCA | 21 |
| NPD009 | NM_020686 | S4476/NPD009.p3 | SEQ ID NO:177 | TTCCCAGAGTGTCTCACCTCCAGCAGAG | 28 |
| PCNA | NM_002592 | S0447/PCNA.f2 | SEQ ID NO:178 | GAAGGTGTTGGAGGCACTCAAG | 22 |
| PCNA | NM_002592 | S0448/PCNA.r2 | SEQ ID NO:179 | GGTTTACACCGCTGGAGCTAA | 21 |
| PCNA | NM_002592 | S4784/PCNA.p2 | SEQ ID NO:180 | ATCCCAGCAGGCCTCGTTGATGAG | 24 |
| PR | NM_000926 | S1336/PR.f6 | SEQ ID NO:181 | GCATCAGGCTGTCATTATGG | 20 |
| PR | NM_000926 | S1337/PR.r6 | SEQ ID NO:182 | AGTAGTTGTGCTGCCCTTCC | 20 |
| PR | NM_000926 | S4743/PR.p6 | SEQ ID NO:183 | TGTCCTTACCTGTGGGAGCTGTAAGGTC | 28 |
| PREP | NM_002726 | S1771/PREP.f1 | SEQ ID NO:184 | GGGACGGTGTTCACATTCAAG | 21 |
| PREP | NM_002726 | S1772/PREP.r1 | SEQ ID NO:185 | CAGGATCCCAGAAGTCAATGTTG | 23 |
| PREP | NM_002726 | S4929/PREP.p1 | SEQ ID NO:186 | TCGCCAGTCTCCCAACTATCGCGT | 24 |
| PTTG1 | NM_004219 | S4525/PTTG1.f2 | SEQ ID NO:187 | GGCTACTCTGATCTATGTTGATAAGGAA | 28 |
| PTTG1 | NM_004219 | S4526/PTTG1.r2 | SEQ ID NO:188 | GCTTCAGCCCATCCTTAGCA | 20 |
| PTTG1 | NM_004219 | S4527/PTTG1.p2 | SEQ ID NO:189 | CACACGGGTGCCTGGTTCTCCA | 22 |
| RPLPO | NM_001002 | S0256/RPLPO.f2 | SEQ ID NO:190 | CCATTCTATCATCAACGGGTACAA | 24 |
| RPLPO | NM_001002 | S0258/RPLPO.r2 | SEQ ID NO:191 | TCAGCAAGTGGGAAGGTGTAATC | 23 |
| RPLPO | NM_001002 | S4744/RPLPO.p2 | SEQ ID NO:192 | TCTCCACAGACAAGGCCAGGACTCG | 25 |
| SNRPF | NM_003095 | S4489/SNRPF.f2 | SEQ ID NO:193 | GGCTGGTCGGCAGAGAGTAG | 20 |
| SNRPF | NM_003095 | S4490/SNRPF.r2 | SEQ ID NO:194 | TGAGGAAAGGTTTGGGATTGA | 21 |
| SNRPF | NM_003095 | S4491/SNRPF.p2 | SEQ ID NO:195 | AAACTCATGTAAACCACGGCCGAATGTTG | 29 |
| Src | NM_004383 | S1820/Src.f2 | SEQ ID NO:196 | CCTGAACATGAAGGAGCTGA | 20 |

TABLE 4D

| | | | | | |
|---|---|---|---|---|---|
| Src | NM_004383 | S1821/Src.r2 | SEQ ID NO:197 | CATCACGTCTCCGAACTCC | 19 |
| Src | NM_004383 | S5034/Src.p2 | SEQ ID NO:198 | TCCCGATGGTCTGCAGCAGCT | 21 |
| STK15 | NM_003600 | S0794/STK15.f2 | SEQ ID NO:199 | CATCTTCCAGGAGGACCACT | 20 |
| STK15 | NM_003600 | S0795/STK15.r2 | SEQ ID NO:200 | TCCGACCTTCAATCATTTCA | 20 |
| STK15 | NM_003600 | S4745/STK15.p2 | SEQ ID NO:201 | CTCTGTGGCACCCTGGACTACCTG | 24 |
| STMY3 | NM_005940 | S2067/STMY3.f3 | SEQ ID NO:202 | CCTGGAGGCTGCAACATACC | 20 |
| STMY3 | NM_005940 | S2068/STMY3.r3 | SEQ ID NO:203 | TACAATGGCTTTGGAGGATAGCA | 23 |

TABLE 4D-continued

| | | | | | |
|---|---|---|---|---|---|
| STMY3 | NM_005940 | S4746/STMY3.p3 | SEQ ID NO:204 | ATCCTCCTGAAGCCCTTTTCGCAGC | 25 |
| SURV | NM_001168 | S02591SURV.f2 | SEQ ID NO:205 | TGTTTTGATTCCCGGGCTTA | 20 |
| SURV | NM_001168 | S0261/SURV.r2 | SEQ ID NO:206 | CAAAGCTGTCAGCTCTAGCAAAAG | 24 |
| SURV | NM_001168 | S4747/SURV.p2 | SEQ ID NO:207 | TGCCTTCTTCCTCCCTCACTTCTCACCT | 28 |
| TFRC | NM_003234 | S1352/TFRC.f3 | SEQ ID NO:208 | GCCAACTGCTTTCATTTGTG | 20 |
| TFRC | NM_003234 | S1353/TFRC.r3 | SEQ ID NO:209 | ACTCAGGCCCATTTCCTTTA | 20 |
| TFRC | NM_003234 | S4748/TFRC.p3 | SEQ ID NO:210 | AGGGATCTGAACCAATACAGAGCAGACA | 28 |
| TOP2A | NM_001067 | S0271/TOP2A.f4 | SEQ ID NO:211 | AATCCAAGGGGAGAGTGAT | 20 |
| TOP2A | NM_001067 | S0273/TOP2A.r4 | SEQ ID NO:212 | GTACAGATTTTGCCCGAGGA | 20 |
| TOP2A | NM_001067 | S4777/TOP2A.p4 | SEQ ID NO:213 | CATATGGACTTTGACTCAGCTGTGGC | 26 |
| TS | NM_001071 | S0280/TS.f1 | SEQ ID NO:214 | GCCTCGGTGTGCCTTTCA | 18 |
| TS | NM_001071 | S0282/TS.r1 | SEQ ID NO:215 | CGTGATGTGCGCAATCATG | 19 |
| TS | NM_001071 | S4780/TS.p1 | SEQ ID NO:216 | CATCGCCAGCTACGCCCTGCTC | 22 |

What is claimed is:

1. A method of predicting the likelihood of long-term survival of an ER positive breast cancer patient without the recurrence of breast cancer, comprising determining the expression level of the RNA transcripts of GRB7 and STMY3 or their expression products in an ER positive breast cancer cell obtained from said patient, normalized against the expression level of all RNA transcripts or their products in said ER positive breast cancer cell, or of a reference set of RNA transcripts or their expression products;

wherein expression of GRB7 and STMY3 indicates a decreased likelihood of long-term survival without breast cancer recurrence.

2. The method of claim 1 wherein said cancer is node negative, ER positive breast cancer.

3. The method of claim 1 wherein said RNA comprises intronic RNA.

4. The method of claim 1 wherein said RNA is isolated from a fixed, wax-embedded breast cancer tissue specimen of said patient.

5. The method of claim 1 wherein said RNA is isolated from core biopsy tissue or fine needle aspirate cells.

6. A method of predicting the likelihood of long-term survival of a patient diagnosed with invasive ER positive breast cancer, without the recurrence of breast cancer, comprising the steps of (a) determining the expression levels of the RNA transcripts GRB7 and STMY3 or their expression products in a breast cancer cell obtained from said patient, normalized against the expression levels of all RNA transcripts or their expression products in said breast cancer cell, or of a reference set of RNA transcripts or their products;

(b) subjecting the data obtained in step (a) to statistical analysis; and;

(c) determining whether the likelihood of said long-term survival has increased or decreased.

7. A method of preparing a personalized genomics profile for a patient diagnosed with an ER positive breast cancer, comprising the steps of (a) subjecting RNA extracted from breast cancer cells obtained from the patient to gene expression analysis;

(b) determining the expression level in the tissue of the RNA transcripts of GRB7 and STMY3, wherein the expression level is normalized against a control gene or genes and optionally is compared to the amount found in a breast cancer reference tissue set; and (c) creating a report summarizing the data obtained by said gene expression analysis wherein the report includes a prediction of the likelihood of long term survival of the patient wherein expression of GRB7 and STMY3 indicates a decreased likelihood of long-term survival without breast cancer recurrence.

8. The method of claim 7 wherein said breast tissue is obtained from a fixed, paraffin-embedded biopsy sample.

9. The method of claim 8 wherein said RNA is fragmented.

10. The method of claim 7 wherein said report includes recommendation for a treatment modality of said patient.

* * * * *